US009138543B2

(12) United States Patent
Frantz et al.

(10) Patent No.: US 9,138,543 B2
(45) Date of Patent: Sep. 22, 2015

(54) INJECTION DEVICE COMPRISING A DOSING MECHANISM FOR LIMITING A DOSAGE SETTING

(75) Inventors: Markus Frantz, Pöring (DE); Peter Stettler, Kirchberg (CH); Malte Kladiwa, Bern (CH); Patrick Hostettler, Hasle-Rüegsau (CH); Kevin Mori, Hasle b. Burgdorf (CH); Aurèle Horisberger, Allschwil (CH); Jürgen Wittmann, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 646 days.

(21) Appl. No.: 13/335,203

(22) Filed: Dec. 22, 2011

(65) Prior Publication Data
US 2012/0245532 A1    Sep. 27, 2012

Related U.S. Application Data

(63) Continuation of application No. PCT/EP2009/057854, filed on Jun. 23, 2009.

(51) Int. Cl.
*A61M 5/30* (2006.01)
*A61M 5/315* (2006.01)
*A61M 5/20* (2006.01)
*A61M 5/24* (2006.01)

(52) U.S. Cl.
CPC .............. *A61M 5/31561* (2013.01); *A61M 5/20* (2013.01); *A61M 5/31551* (2013.01); *A61M 5/31583* (2013.01); *A61M 5/24* (2013.01); *A61M 5/31541* (2013.01); *A61M 5/31543* (2013.01)

(58) Field of Classification Search
CPC ............... A61M 5/31541; A61M 5/31543; A61M 5/31551; A61M 5/31561; A61M 5/31583
USPC ................... 604/211, 207, 208, 218
See application file for complete search history.

(56) References Cited

U.S. PATENT DOCUMENTS

| 3,202,151 | A | 8/1965 | Kath | |
|---|---|---|---|---|
| 8,048,037 | B2 | 11/2011 | Kohlbrenner | |
| 2009/0254044 | A1* | 10/2009 | Kohlbrenner et al. | 604/207 |
| 2011/0270214 | A1* | 11/2011 | Jorgensen et al. | 604/500 |
| 2014/0074041 | A1* | 3/2014 | Pedersen et al. | 604/211 |

(Continued)

FOREIGN PATENT DOCUMENTS

| EP | 1944050 | 7/2008 |
|---|---|---|
| EP | 2011531 | 1/2009 |
| WO | WO 2007/017053 | 2/2007 |

(Continued)

*Primary Examiner* — Aarti B Berdichevsky
(74) *Attorney, Agent, or Firm* — Dorsey & Whitney LLP; Stuart R. Hemphill, Esq.

(57) ABSTRACT

An injection device including a dosage setting element and a first element which is coupled to the dosage setting element and can be rotated relative to another, second element when a dosage is being set and is rotationally fixed relative to the second element when a dosage is being delivered, wherein the first element and the second element are coupled via a coupling member, and a stop abutment, wherein when a dosage is being set, the coupling member performs a movement toward a stop position, wherein the coupling member prevents a dosage from being set when it is in the stop position.

19 Claims, 15 Drawing Sheets

(56) References Cited

U.S. PATENT DOCUMENTS

2014/0312074 A1* 10/2014 Madsen et al. ............... 222/333
2015/0105732 A1* 4/2015 Kjeldsen et al. ............. 604/207

FOREIGN PATENT DOCUMENTS

| WO | WO 2008/031238 | 3/2008 |
| WO | WO 2009/105909 | 9/2009 |

* cited by examiner

US 9,138,543 B2

INJECTION DEVICE COMPRISING A DOSING MECHANISM FOR LIMITING A DOSAGE SETTING

CROSS-REFERENCE TO RELATED APPLICATIONS

This application is a Continuation of International Patent Application No. PCT/EP2009/057854 filed 23 Jun. 2009, the contents of which are hereby incorporated by reference.

BACKGROUND

The present invention relates to devices for administering, injecting, infusing, delivering or dispensing a substance or product, and to methods of making and using such devices. More particularly, the invention relates to a mechanism for an injection device which prevents a dosage or dose from being set which exceeds the amount of a product to be administered in a product container of the injection device. The product or substance to be administered can be a liquid drug, e.g. insulin.

Using injection devices known from the prior art, dosages can be set using a dosage setting mechanism and then delivered from a product container. It can occur that a larger dosage has been set using the dosage setting element than can be delivered from the product container, for example because the product container contains a smaller dosage than the dosage which has been set. This can have the result that less product is delivered than was set, which depending on the discrepancy can result in more or less severe problems for the patient.

A dosing mechanism for an injection device for preventing a dosage from being set which exceeds the amount of drug in a reservoir of an injection device is known from the prior art. Such devices often have the problem that they take up a relatively large amount of space in the injection device, whereas
the market demands manageably sized injection devices.

SUMMARY

Any reference to "the invention" or "the present invention" in this application shall not be construed as a generalization, limitation or characterization of any subject matter disclosed herein and shall not be considered to be an element or limitation of the appended claims except if and/or where explicitly recited in a claim(s).

It is an object of the present invention to provide a compactly designed mechanism for preventing a dosage from being set which exceeds the amount of a substance or product contained in the product container of an injection device.

In one embodiment, the present invention comprises an injection device comprising a dosage setting element, a first element, a second element, a coupling member and a stop abutment, wherein the first element and the second element are coupled via the coupling member and the first element is coupled to the dosage setting element and rotatable relative to the second element when a dosage is being set and rotationally fixed relative to the second element when a dosage is being delivered, and wherein when a dosage is being set, the coupling member performs a movement toward a stop position involving the stop abutment, the coupling member preventing a dosage from being set when it is in the stop position.

In one embodiment, the present invention comprises an injection device comprising a dosage setting element and a first element which is coupled to the dosage setting element and can be rotated relative to another, second element when a dosage is being set and is rotationally fixed relative to the second element when a dosage is being delivered, wherein the first element and the second element are coupled via a coupling member which can also be referred to and/or thought of as a stop or stop member. The dosage setting element can be rotated and can be able to be moved, axially fixed or longitudinally, relative to the housing. The dosage setting element can perform a longitudinal movement when rotated, such as a screwing movement. The dosage setting element can be rotated by the user of the device in at least one direction relative to the housing for setting a dosage, e.g. in a first rotational direction for increasing the dosage and in a second rotational direction, opposite to the first rotational direction, for decreasing the dosage. The latter function can also be referred to and/or thought of as correcting the dosage. The dosage setting element can be sleeve-shaped and can be situated in the region of the proximal end of the injection device. Alternatively or additionally, the dosage setting element can be arranged within the housing of the device, wherein the housing and the dosage setting element can be sleeve-shaped. It is conceivable for the user to not have direct access to the dosage setting element, but rather to have access via additional parts. The dosage setting element can in principle be formed from a plurality of parts consisting of, for example, parts which are rotationally or translationally moved with respect to each other, wherein a dosage setting element consisting of one part is also conceivable. The dosage setting element situated within the housing can be a dosage indicating sleeve which can be read from outside the housing through an opening or window.

In some embodiments, the first rotatable element and/or second rotatable element are sleeve-shaped and/or can rotate about a common axis, wherein this axis points, for example, in the longitudinal direction of the injection device or in the direction of the needle. The first element and second element can be arranged concentrically with respect to each other, wherein the first element surrounds the second element or forms a passage for the second element. An annular gap can be arranged between the first element and the second element, wherein the coupling member can, for example, be arranged in the annular gap.

In some embodiments, the dosage setting element can be directly or indirectly coupled to the first element. The dosage setting element may be coupled, rotationally fixed, to the first element when the dosage is being set. This coupling can, for example, be released, via a coupler, when the product dosage set is being delivered. Alternatively, the dosage setting element can be permanently coupled, rotationally fixed, to the first element, if the dosage setting element is a dosage indicating sleeve, wherein the dosage indicating sleeve can then be able to be axially shifted relative to the first element.

Because the first element can be rotated relative to the second element when a dosage or dose is being set or selected, the coupling member can perform a relative movement relative to the first element and/or relative to the second element. Because the first element is rotationally fixed relative to the second element when the dosage is being delivered, a movement of the coupling member relative to the first element and relative to the second element can be prevented. The first element, the second element and the coupling member can, for example, be rotated together, relative to the housing, when the dosage is being delivered. In some preferred embodiments, a coupler is provided which is in a first coupler state when the dosage is being set and is in a second coupler state when the dosage is being delivered. The coupler can be connected to the first element and to the second element in such a way that the first element can rotate relative to the second element in the first coupler state, for example in the open coupler state, wherein the first element is rotationally fixed relative to the second element in the second coupler state, e.g. in the closed coupler state. The user can activate the coupler to establish the desired coupler state, depending on whether the user wishes to set or deliver a dosage.

In some preferred embodiments, the coupling member can engage with the first element and the second element in a positive fit. The first element and the second element can each comprise a guiding track with which the coupling member engages. The guiding tracks can be configured to be thread-shaped or helical or can be embodied as a longitudinal guide which runs approximately parallel to the longitudinal direction of the injection device or the rotational axis of the first or second element. In some preferred embodiments, at least one of the guiding tracks is thread-shaped or helical. The pitches for the threads of the first and second element can be of different sizes and/or opposites, wherein in the latter case, the threads or helices exhibit opposite directions of rotation. The guiding tracks of the first element and second element opposite each other. The guiding track of the first element can for example be formed on the inner circumference of the first element, for example as a thread or inner thread, and the guiding track of the second element can for example be formed on the outer circumference of the second element as a thread or outer thread. In some embodiments, the guiding tracks of the first element and the second element should not interlock, i.e. they should not mesh. Only the coupling member—although a plurality of coupling members can be provided—couples the guiding track of the first element to the guiding track of the second element.

In some preferred embodiments, the coupling member can be a sphere, a ring, a nut—e.g. a stop nut—or a segment. A sphere may have an advantage in that it does not need to comprise an engaging member which is specifically fitted for the engagement with the guiding tracks, but rather couples the first element and the second element in all of its possible positions due to its rotationally symmetrical shape, i.e. the sphere does not need to be aligned in a specific way. The cross-sectional shape of the guiding tracks can be adapted to the contour of the sphere. In some embodiments, at least one of the guiding tracks—or both guiding tracks—can be concave and/or rounded and/or approximately circular in cross-section.

A ring, or a nut which exhibits an annular cross-section, forms a passage for the second element and supports the second element toward the first element in all directions transverse to the longitudinal axis. Corresponding engaging elements, such as for example threaded portions, are formed on the outer and inner circumference of the nut for each of the guiding tracks, for the engagement with the respective guiding track.

A segment-shaped coupling member, which can be a segment of the stop nut, has the advantage that the annular space is not completely filled, which saves material on the one hand and design space on the other. In certain circumstances, such a segment can be easy to install.

In other embodiments, the coupling member can be formed from a plurality of parts, such as by two parts which are connected to each other such that they are axially fixed and can be rotated relative to each other, one of which is configured such that it engages with the guiding tracks and the other of which, for example, comprises an abutment which for example passes into an engagement with a stop abutment, which is described below, to prevent any further dosage setting. The parts which form the coupling member can be rotated relative to each other by a selected angle which may be smaller than 360° and or smaller than 180°. When moving with respect to each other, the two interlocking parts can produce at least one and, in some preferred embodiments, a multitude of audible or tangible clicks by a latching element, which indicate to the user of the device that the stop position has been reached. The click can be produced as the stop position is reached or before the stop position is reached and can sound or feel different to other clicks produced by the device. The click is produced when the dosage setting element is rotated further by the angle by which the two parts of the coupling member can be rotated relative to each other. It is thus indicated that said stop position has been reached. The two parts of the coupling member can be biased against each other using a spring. This can ensure that the two parts can be rotated with respect to each other by the angle, wherein this angle is reduced and the two parts are rotated relative to each other against the spring force when the coupling member is in abutment with a stop abutment.

In some embodiments, the injection device also comprises a stop abutment, wherein when a dosage is being set, the coupling member performs a movement toward the stop position, toward the stop abutment, wherein the coupling member prevents a dosage from being set when it is in the stop position, when it is in abutment with the stop abutment. It is possible to prevent the dosage from being increased, wherein it is possible to correct, i.e. reduce, the dosage, for example because the coupling member is moved away from the stop abutment. In some preferred embodiments, the coupling member cannot perform any movement toward or away from the stop position when the dosage is being delivered. The stop abutment can be formed by at least one of the first element—e.g. an element which is connected, rotationally fixed or axially fixed, to the first element—and the second element—e.g. an element which is connected, axially fixed or rotationally fixed, to the second element. The end of the guiding track or guiding tracks can for example each form a stop abutment.

The stop abutment can in principle act in the axial direction, wherein in some preferred embodiments, the stop abutment acts in the rotational direction. An abutment which acts in the rotational direction acts directly counter to the rotational direction. If an abutment acts in the axial direction, the rotational movement is translated into a pressing force onto the abutment. The pressing force of the stop abutment is thus greater onto an abutment which acts in the axial direction than onto an abutment which acts in the rotational direction.

In some embodiments, a plurality of dosage settings and deliveries are possible using the arrangement in accordance with the present invention, wherein the coupling member is moved slightly nearer to the stop abutment with each dosage setting. The distance which the coupling member exhibits from the stop position corresponds to the contents which the product container contains.

An example will help illustrate the use or application: a product container can contain 300 units of insulin when completely filled. Values from 1 to 60 or 80 can in principle be respectively set in increments of one or two with each individual dosage setting. When a product container is completely filled, the coupling member is a path away from the stop position, wherein this path can be sub-divided into the number of units contained in the product container, such as in this example 300 units. With each dosage setting, the coupling member is moved a distance in the direction of the stop position which corresponds to the dosage set. If, for example, 295 units are delivered from the product container, then 5 units still remain in the product container. Correspondingly, the coupling member is also 5 units away from the stop position. Although 60 or 80 units can in principle be set for each dosage setting using the dosage setting element, the dosage setting element can only increase the dosage by 5 units in this case, since the coupling member then enters into abutment with the stop abutment, thus preventing the dosage from being increased. This can reduce the danger of the injection device being incorrectly used.

In some preferred embodiments, the coupling member can be coupled to the first element and to the second element in such a way that when the first element is moved relative to the second element, the coupling member can be or is rotated relative to at least one and, in some embodiments, both of the first element and the second element. When the first element is rotated relative to the second element, the coupling member can for example be rotationally fixed to either the first or second element and can be rotated together with the first or second element relative to the other of the first and second element. To this end, the coupling member can engage with a longitudinal guide which is formed on the element relative to which the coupling member is rotationally fixed when the dosage is being set. The coupling member can also engage with a thread-shaped guiding track, e.g. a thread, which is formed on the element relative to which the coupling member is rotated together with the other element when the dosage is being set.

In the embodiment in which the coupling member is rotated relative to the first element and relative to the second element when the first element is rotated relative to the second element, the coupling member can engage with the thread of the first element and with the thread of the second element. During a rotation, the coupling member is thus rotated continuously or with a gearing increase or with a gearing decrease, about the longitudinal axis about which the first and second element can be rotated. An advantage of this is that irrespective of whether the dosage setting element or the first element performs a quarter revolution, a half revolution, a complete revolution or a plurality of revolutions relative to the second element, the coupling member performs a rotational movement relative to the first element and relative to the second element. The present invention differs in this respect from counting rings, in which for example a units counting ring is rotated by a full revolution relative to a tens counting ring and at the end of the full revolution, slaves the tens counting ring by one unit. The part of the units counting ring which slaves the tens counting ring does not perform a movement relative to the tens counting ring but rather to the tens counting ring and only then when the units counting ring does not slave the tens counting ring.

Another advantage of the invention is that when the first element is rotated relative to the second element, the coupling member is rotated along with it by a rotational angle which is greater or smaller than the rotational angle of the first element. This also applies to the rotational angular speed, i.e. when the first element is rotated relative to the second element, the coupling member is rotated along with it relative to the housing by a rotational angular speed which is higher or lower than the rotational angular speed of the first element. In some preferred embodiments, the rotational angle or the rotational angular speed of the coupling member is higher than that of the second element, since the latter is stationary with respect to the housing when the dosage is being set.

The rotational angle or the rotational angular speed of the coupling member which it exhibits when the first element is rotated relative to the second element or the housing is, for example, higher when the threads or helices exhibit the same direction of rotation and the pitch of the guiding track of the first element is greater than the pitch of the guiding track of the second element. The coupling member exhibits a smaller rotational angle or a slower rotational angular speed relative to the second element or the housing than the first element exhibits relative to the second element or the housing, wherein the rotational direction of the coupling member is opposite to the rotational direction of the first element relative to the second element when the threads or helices exhibit the same direction of rotation and the guiding track of the first element exhibits a smaller pitch than the guiding track of the second element. The guiding tracks of the first element and second element can in principle exhibit the same direction of rotation and the same pitches.

In some embodiments, the coupling member can rotate relative to the second element or the housing in the same rotational direction and by a smaller rotational angle or a lower rotational angular speed than the first element relative to the second element or the housing when the threads or helical guiding tracks of the first element and second element exhibit opposite directions of rotation. The pitches of the guiding tracks of the first element and second element can be equal in size or the pitch of the guiding track of the first element can be greater than that of the second element, or vice versa.

In some embodiments, the pitches of the threads or helical guiding tracks can be very small or very large, wherein if the pitch is finite in size, the guiding track is a guiding track and/or longitudinal guiding track which extends along the rotational axis, i.e. parallel to the rotational axis.

In some embodiments, the first rotatable element can be connected to a spring, e.g. a torsion spring, which stores the energy necessary for delivering the dosage and dispenses it as required. The spring can be tensed by the dosage setting movement of the dosage setting element or the first element. The spring can in principle be helical or spiral. The spring can be wound from a wire or from a ribbon-shaped material, e.g. spring steel. Such springs may be referred to as clock springs. At least one of the dosage indicating sleeve, the first element and the dosage setting element can be coupled, rotationally fixed, to one end of the spring when the dosage is being set, wherein the other end of the spring is connected to the housing. For delivering the dosage, the first element and/or the dosage indicating sleeve can be coupled, rotationally fixed, to one end of the spring, wherein the dosage setting element is, for example, decoupled.

In some embodiments, the dosage indicating sleeve can for example comprise a thread, e.g. an inner thread or outer thread, which engages with the housing or with an element which is fixedly connected to the housing, to be able to perform a screwing movement to indicate the dosage. To this end, the dosage indicating sleeve can comprise a helical scale which is arranged on its outer circumference. The dosage indicating sleeve can comprise abutments, e.g. abutments which act in the axial direction or in the circumferential direction, which can abut corresponding counter abutments of for example the housing. The dosage indicating sleeve can be moved back and forth between these abutments, such that dosages from zero to the desired maximum dosage, such as for example 60 or 80 units, can be set using the dosage indicating sleeve, providing the coupling member is not situated in the stop position. A maximum dosage which can be set can thus be limited on the one hand by the abutment of the dosage indicating sleeve or by the coupling member, depending on which of the two elements prevents the dosage from being increased first.

As may be preferred in some embodiments, the second rotatable element can be coupled, rotationally fixed, to a driven member, e.g a piston rod, wherein the driven member can be screwed in the delivery direction to deliver a product. To this end, the driven member can comprise a thread via which it engages with the housing or with an element which is fixedly connected to the housing, to be able to perform the screwing movement. The second rotatable element can be the piston rod. In some preferred embodiments, the second rotatable element is sleeve-shaped and coupled, rotationally fixed, to the driven member, wherein the driven member can perform a longitudinal movement relative to the second rotatable element. The second rotatable element can be coupled directly or indirectly to the driven member. The second element can be coupled, rotationally fixed or such that it can be longitudinally shifted, to the driven member via a sleeve, e.g. a coupler sleeve. The second element can be coupled, rotationally fixed and such that it can be longitudinally shifted, to the sleeve which is arranged between the driven member and the second element, for example via longitudinal grooves. This has the advantage that when a product container is changed, the second element does not need to perform or does not perform an axial movement relative to the first element, wherein the driven member and as applicable the sleeve which surrounds the driven member can be able to be axially moved relative to the second element. The sleeve which directly engages with the driven member can be the second element.

In some preferred embodiments, at least one of the first element and the second element can comprise a thread-shaped guiding track or groove, and the other of the first element and the second element can comprise a guiding track or groove which is thread-shaped or which extends parallel to the longitudinal axis, wherein the coupling member—e.g. its center of gravity—is arranged where the guiding tracks or grooves intersect, in their projection. The annular gap between the first element and the second element may be relatively thin. The guiding tracks or grooves can form an enclosure for the coupling member which encloses the coupling member at least such that it remains where the guiding tracks intersect. The coupling member can be able to be freely moved in this enclosure within a greater or smaller clearance. In the projection of the two guiding tracks, the enclosure can for example be parallelogram-shaped, e.g. rectangular, square or rhombic. The mutually opposing edges of the parallelogram are each formed by one of the guiding tracks. The enclosure ensures that the coupling member remains where the guiding tracks intersect. When the first element is rotated relative to the second element, the enclosure and therefore the coupling member situated in the enclosure moves relative to the first and/or second element. In some preferred embodiments, the coupling member is guided toward the stop position by the enclosure when a dosage is being increased and away from the stop position when a dosage is being reduced. The guiding track of the first element forms a first partial enclosure, and the guiding track of the second element forms a second partial enclosure, which together form the enclosure for the coupling member. The coupling member can be arranged substantially completely within the enclosure; at least the geometric center of gravity or the centre of mass of the coupling member is arranged within the enclosure. A spherical coupling member may be advantageous here, although other rotationally symmetrical bodies such as, for example, a cylindrical body could be considered, e.g. if one of the two guiding tracks is a longitudinal guide. Other bodies which fit into the enclosure, such as cubes, or bodies which exhibit a parallelogram-shaped cross-section, e.g. a rhombic, rectangular or square cross-section, are also conceivable. Generally, the stop abutment which the coupling member abuts in the stop position is adapted to the abutment surface of the coupling member, to produce as much surface pressing as possible. For a spherical coupling member, for example, the stop abutment can be a part of a spherical shell which exhibits the same radius as the spherical coupling member.

In some preferred embodiments, at least one of the guiding tracks or grooves forms an abutment which acts in the axial direction or circumferential direction, i.e. the stop abutment, for the coupling member. The end of the guiding track of the first element can abut the coupling member in the stop position, wherein the coupling member abuts the end of the guiding track of the second element. The coupling member can be clamped between the ends of the guiding tracks of the first and second element. The first element is prevented from rotating relative to the second element to increase a dosage. A flank of one of the longitudinal guides could also in principle form an abutment, and this may be preferred in some embodiments if a guiding track is formed as a longitudinal guide.

In some preferred embodiments, the coupling member can extend over only a part of the circumference of the second rotatable element. Such a coupling member can in principle be one of the aforementioned bodies provided for the enclosure, wherein the coupling member extends in the shape of a segment over the circumference of the second rotatable element. The segment can be a part of the circumference of a nut. The two ends which point in the circumferential direction, i.e. the opposite ends of the segment-shaped coupling member, can encompass the second rotatable element to such an extent that the connecting straight line through the two ends passes or is tangential to the circumference of the driven member which is mounted by the second element, for example the piston rod. Because the segment does not form a passage for the driven member, it is possible to save space in the annular gap between the first and the second element. An advantage of this is that other parts of the injection device can be arranged in the annular gap, thus enabling the injection device as a whole to be designed more compactly. The segment can also, in the same way as a nut, comprise an abutment on its facing surface for the stop abutment, which points or acts in the rotational direction.

In some preferred embodiments, a supporting member can be arranged in the annular gap, opposite the coupling member in relation to the circumference of the second element. The supporting member can be inserted into the annular gap as a separate part or formed on one of the first element, the second element and the coupling member. The supporting member can be formed on the second element and protrude into the annular gap, wherein the coupling member is longitudinally guided on the second element, wherein the supporting member can be supported on the inner circumference of the first element and/or can slide along the inner circumference of the first element. Alternatively, the supporting member can be formed on the first element and protrude into the annular gap, wherein the coupling member is longitudinally guided on the first element and the supporting member can be supported on the outer circumference of the second element and can slide along the outer circumference of the second element. A supporting member can ensure that if the device is used improperly, for example if the user violently twists the dosage setting element, the first or second element cannot be ejected from their concentric arrangements if the coupling member is pressed heavily onto the stop abutment.

As an alternative to the supporting member or in addition to the supporting member, the abutment of the coupling member or the stop abutment or both can exhibit a corresponding shape which prevents the first and/or second element from being ejected from its rotational axis.

In some preferred embodiments, the coupling member can be connected to a base element in a force fit, a positive fit and/or a material fit, comprising at least one predetermined breaking point, wherein this connection can be released when the first element is rotated relative to the second element for the first time. The base element can for example be arranged in the annular gap between the first element and the second element. An embodiment in which the base element forms the supporting member is also possible. In an initial position, before the injection device is used for the first time, the base element and the coupling member can be formed in one part, by an injection-moulding process. Stays for forming predetermined breaking points can be provided which break when the first element is moved relative to the second element, for example by axially or rotationally moving the coupling member relative to the base element. The base element advantageously serves as an installing aid for the coupling member, e.g. the segment-shaped coupling member.

In some preferred embodiments, the coupling member can extend at least partially, e.g. completely, over the circumference of the second rotatable element, for example forming a nut. In this embodiment, two thread-shaped guiding tracks may be provided. For some embodiments, it may be preferred if the pitch of one of the two thread-shaped guiding tracks, with which the coupling member engages, is greater than the pitch of the other of the two thread-shaped guiding tracks. In accordance with the examples of the intersecting guiding tracks as mentioned here, an identical or opposite direction of rotation or a gearing increase or gearing decrease can be produced for the coupling member, wherein the movement of the coupling member is continuous.

The rotation of the coupling member relative to the first element or relative to the second element can be smaller than one full revolution when the coupling member is moved into the stop position from the position in which it is at its furthest from the stop position, and at least one of the guiding tracks can exhibit a very large thread pitch for this purpose. A friction situation in the injection device is thus achieved. The coupling member may be at its furthest from the stop position when a product container is full.

In some preferred embodiments, the guiding track exhibits a width which expands or tapers toward the stop position, thus enabling a clearance for the coupling member when moving into the stop position to be increased or reduced, wherein this also results in advantages in the manufacture of the second element, for example when removing it from an injection-moulding die.

DETAILED DESCRIPTION

With regard to fastening, mounting, attaching or connecting components of the present invention, unless specifically described as otherwise, suitable mechanical fasteners and methods may be used. Other appropriate fastening or attachment methods include adhesives, welding and soldering, the latter particularly with regard to the electrical system(s) of the invention, if any. Suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
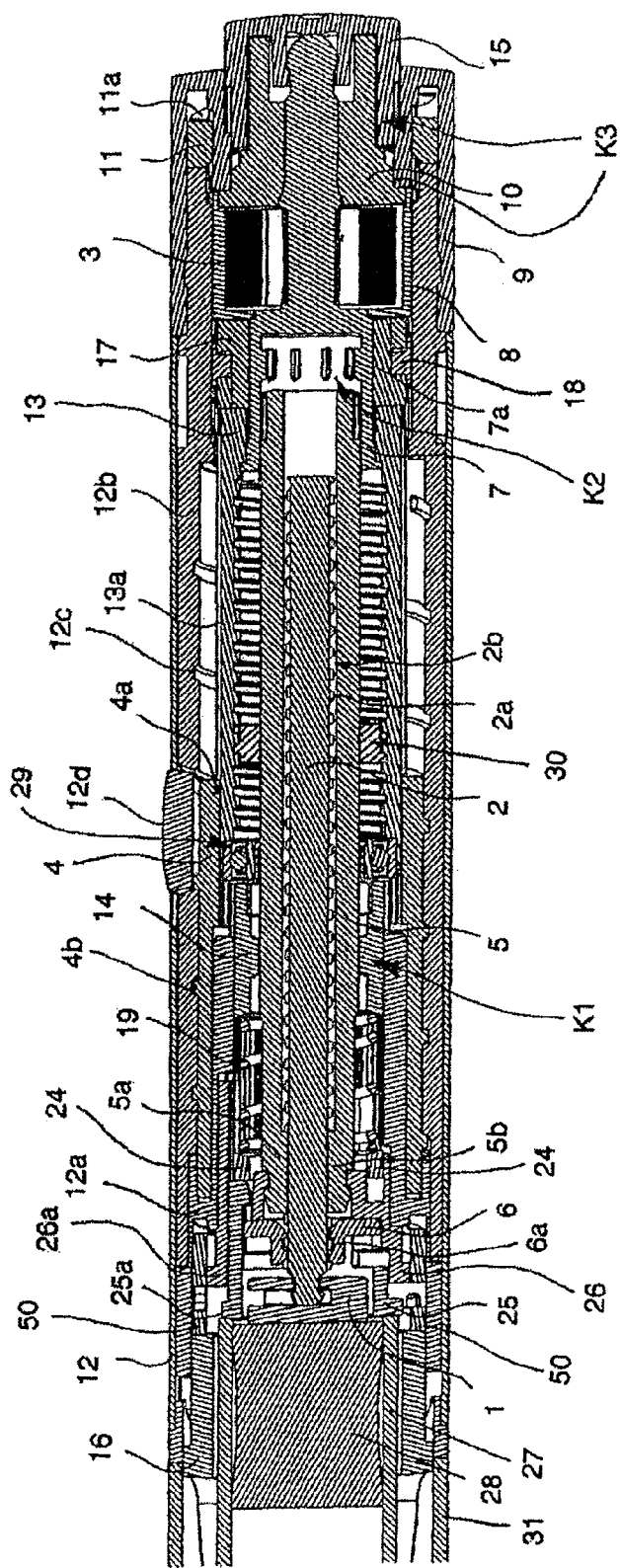
FIG. 1 is a cross-sectional view of a proximal part of an embodiment of an injection device in accordance with the present invention.

The injection device shown in FIG. 1 comprises a drive unit, which can be used repeatedly, and a product container 27 which is connected to the drive unit and accommodated in a sleeve-shaped product container receptacle 16, which can be used repeatedly, and can be fastened to the drive unit with the aid of the product container receptacle 16. Once it has been emptied, the product container 27 can be removed from the injection device, disposed of and replaced with a new product container. The housing 12 is formed from a plurality of parts, since this may make it easier to manufacture and install, comprising elements 12a, 12b which are connected to it or inserted, wherein the housing could also in principle be formed in one part. The product container 27 is fastened to the drive unit with the aid of bayonet lock which is formed by the housing 12, the product container receptacle 16 and the sleeve 50. The product container receptacle 16 is covered by a cap 31 which is affixed to the housing 12 and can be removed for using the injection device and then re-affixed.

To attach the product container 27 to the drive unit, a new product container 27 is inserted into the product container receptacle 16 through the proximal end. The product container receptacle 16 is then affixed to the sleeve 50, with zero torque, using an axial movement or a combined rotational and axial movement.

A guiding sleeve 26 is accommodated in the sleeve 50, which can also be referred to and/or thought of as the bayonet sleeve. The guiding sleeve 26 is connected, rotationally fixed and such that it can be axially moved, to the housing 12 and is connected, axially fixed and such that it can be rotated, to the bayonet sleeve 50. This means that when the bayonet sleeve 50 is moved from the unlocked position to the locked position and vice versa, the guiding sleeve 26 performs a longitudinally guided movement relative to the housing 12.

As can be seen in FIG. 1, a threaded insert 6 is connected and latched, rotationally and axially fixed, to the guiding sleeve 26. The threaded insert 6 and the guiding sleeve 26 can be referred to and/or thought of as an engaging member. The threaded insert 6 comprises an inner thread 6a in which the outer thread 2a of a driven member 2—which in this example can also be referred to as a piston rod—is guided, such that when the driven member 2 is rotated, it is screwed—while being guided by the inner thread 6a of the threaded insert 6—in either the proximal direction or the distal direction, i.e. the opposite direction, depending on the rotational direction.

The driven member 2 bears or carries a thread 2a on its outer side which is interrupted by two grooves 2b which lie opposite each other on the circumference and run or extend in the axial direction. A coupler sleeve 5, which is part of a transmission element (comprising elements 7, K2, 5), has two projections 5a, 5b at its distal end which lie opposite each other and are directed radially inward and protrude into the grooves 2b of the driven member 2. The coupler sleeve 5 is connected, axially fixed and such that it can be rotated, to the engaging member 6, 26. The driven member 2 is thus secured against rotating relative to the coupler sleeve 5 and can be axially moved relative to the coupler sleeve 5 when it is rotated relative to the engaging member 6, 26. The coupler sleeve 5 cannot be axially shifted, except for when the product container 27 is being replaced.

A drive shaft 7 which is provided on the proximal end of the injection device and is part of the transmission element comprises teeth 7a which protrude radially inward and form a coupler element of the coupler K2. Activating, i.e. pressing, an activation element 15 in the distal direction shifts the drive shaft 7 and therefore also the teeth 7a in the distal direction, whereby the teeth 7a engage with the proximal end of the coupler sleeve 5 and form a zero-torque and positive-fit connection.

A spring element and/or drive spring 3, which can be formed as a spiral spring or clock spring, is connected at one end to the housing 12 via a spring sleeve 8 on the outer side of the spring element 3. The spring sleeve 8 is secured against rotating relative to the housing 12 and can be axially shifted relative to the housing 12. At its other end, the drive spring 3 is connected to the drive shaft 7. Energy stored in the spring element 3 can thus be dispensed as a rotational movement of the drive shaft 7 relative to the housing 12. To deliver a product, the energy of the spring element 3 is dispensed to the driven member via the transmission element 5, K2, 7 in the form of a rotational movement, such that the driven member is screwed relative to the engaging member 6, 26 in the distal direction, i.e. in the delivery direction, and shifts the piston 28 which delivers the product from the product container 27.

To set or select a product dosage to be administered, a user can rotate the dosing element 9 which is configured as a dosing button and is axially fixed relative to the housing 12. The dosing element 9 is coupled, secured against rotating, to a coupler member 10 via the coupler K3. The coupler K3 is formed by stays or grooves or teeth of the dosing button 9 which co-operate in a positive fit with stays or grooves or teeth of the coupler member 10 to form a coupler which can be released by shifting the coupler member 10 in the distal direction. The coupler member 10 can be shifted and thus released by activating the activation element 15. In a non-activated state, the coupler K3 is held in a coupled state and the coupler K2 is held in a decoupled state by a spring element 19 which presses the drive shaft 7 in the proximal direction. The coupler K3 is coupled during the dosage setting process, i.e. a rotational movement of the dosing button 9 is transmitted onto the coupler member 10. The coupler member 10 is connected, axially and rotationally fixed, to the drive shaft 7 and could also be formed in one part together with the drive shaft 7. Because the coupler K2 is decoupled, the rotational movement of the dosing member 9 is not transmitted onto the coupler sleeve 5.

Rotating the drive shaft 7 tenses the drive spring 3 which is connected to the drive shaft 7. To prevent the drive spring 3, which is tensed during the setting process, from rotating the dosing button 9 back again, a ratchet 11 or ratchet mechanism which can comprise a ratchet spring 11a, for example for tensing holding elements, is provided between the housing 12 of the injection device, the components of which can for example be a mechanism holder 12a and a mechanism holder 12b, and the dosing button 9. The ratchet mechanism can be configured such that rotation is only possible in one direction, such that it is only possible to tense the drive spring 3. In some preferred embodiments, however, the ratchet mechanism is configured such that rotation is possible in both rotational directions, such that it is possible to tense and relax the drive spring 3. If rotation is possible in both directions, this enables a product dosage to be both increased and reduced when setting the product dosage. The currently set product dosage can be read off from an indicating drum 4 via the window 12d.

The rotational movement of the drive shaft 7 is also transmitted onto the threaded sleeve 13 which is connected, rotationally and axially fixed, to the drive shaft 7 and could also be formed in one part together with the drive shaft 7. The threaded sleeve 13 bears at least one groove on its outer circumference 13a, with which at least one stay 4a of the indicating drum 4 engages, such that a rotational movement of the threaded sleeve 13 is transmitted onto the indicating drum 4 by the rotationally secure coupling, wherein an axial relative movement between the indicating drum 4 and the threaded sleeve 13 is possible. The indicating drum 4 comprises a thread 4b on its outer side which engages with an inner thread 12c of the housing part 12b, such that the indicating drum 4 is shifted in the axial direction relative to the housing 12, in the distal direction, by a rotational movement. The indicating drum 4 is moved in the distal direction of the injection device (to the left in FIG. 1) during a setting or dosage-increasing process by rotating the dosing button 9. A marking such as an inscription, a dosage indicator or a scale can be provided on the outer side of the indicating drum 4 and can be read off through an opening or window 12d in the housing 12 of the injection device, wherein the marking of the indicating drum 4 is shifted relative to the window 12d. The distal end of the indicating drum 4 comprises a rotational abutment which acts in the circumferential direction and enters into abutment with a counter abutment, which is correspondingly formed on the housing part 12a, when a maximum dosage is reached. The counter abutment is formed by a facing-side end of an annular gap of the housing part 12a. An abutment which acts in the circumferential direction has the advantage over an axial abutment that smaller forces act on the abutment. Furthermore, the proximal end of the indicating drum 4 comprises another rotational abutment which acts in the circumferential direction and enters into abutment with a counter abutment, which is correspondingly formed on the housing part 12b, when a minimum dosage is reached. The counter abutment is formed by the proximal end of the flight 12c.

The setting process is complete once the dosage has been set and the drive spring 3 has been drawn up by rotating the dosing button 9, wherein the spring 3 is tensed as the dosage is being increased. To correct or adjust the dosage, the dosing button 9 can be rotated in the opposite direction, to reduce back a dosage which may be have been set too high.

Figure 14:
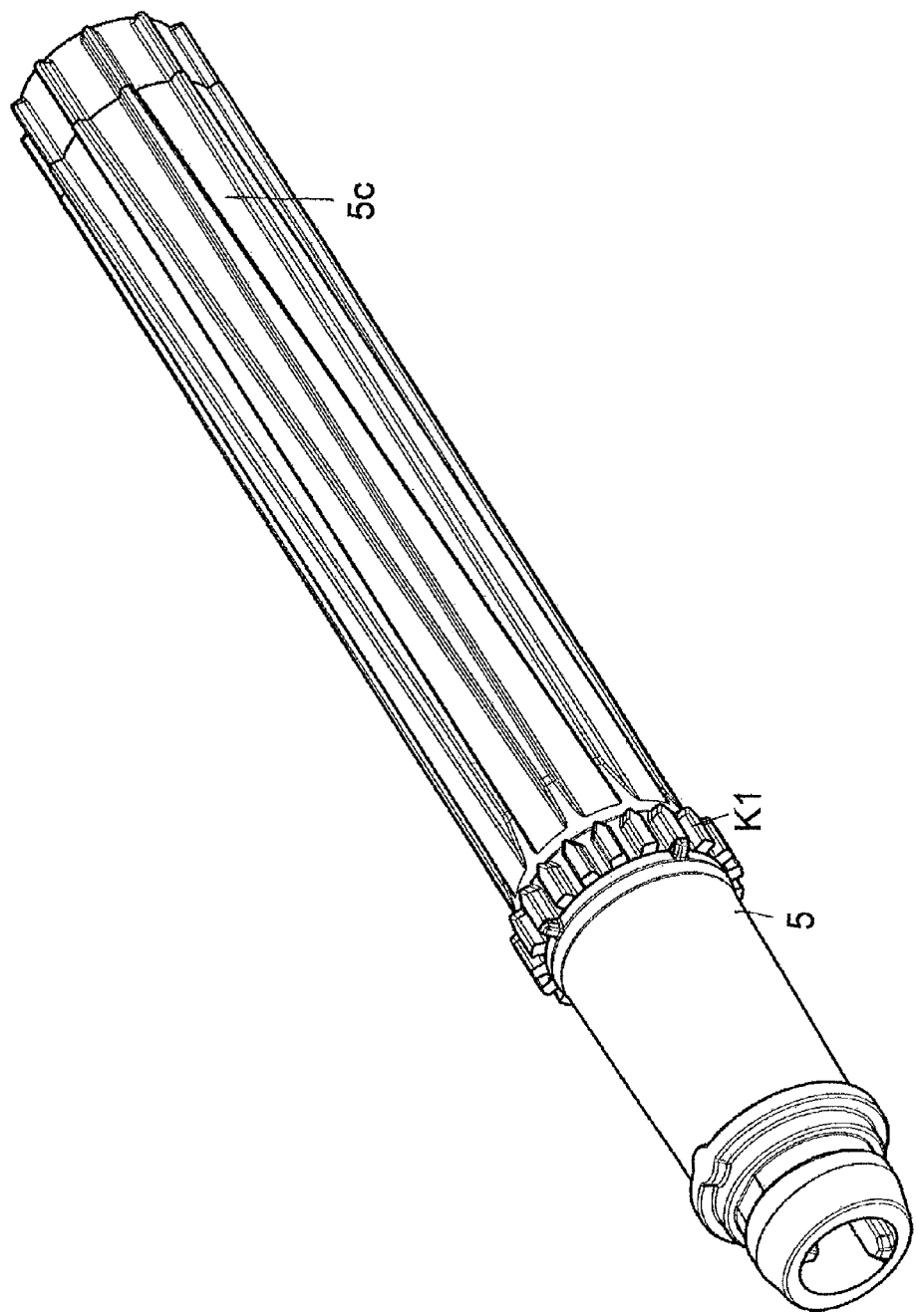
FIG. 14 is a perspective view of another modification of the device of FIG. 1.
Figure 15:
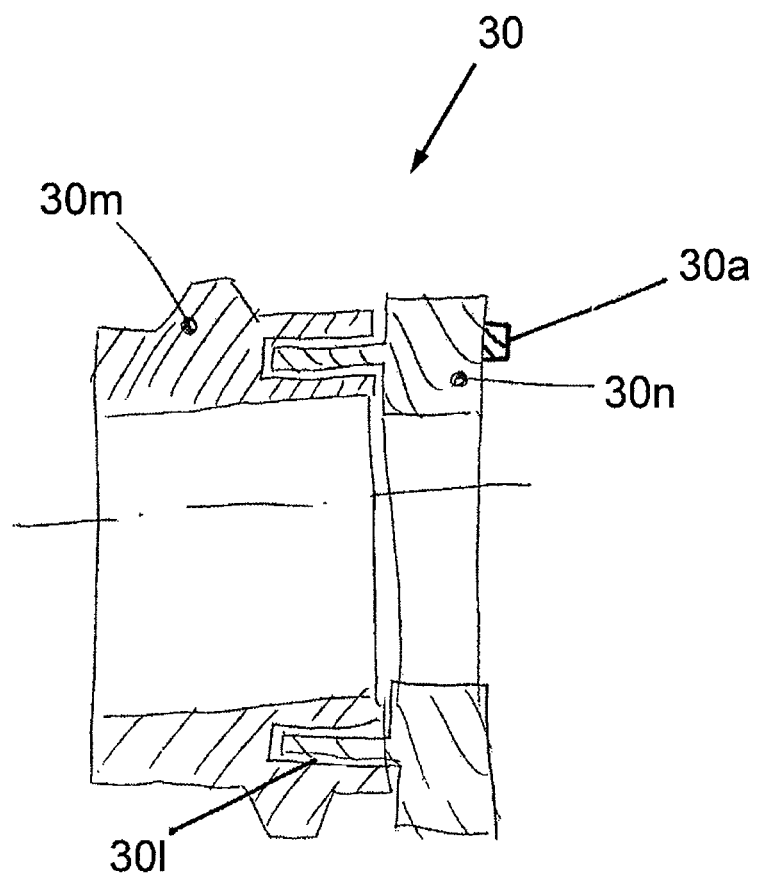
FIG. 15 is a cross-sectional view of an embodiment of a coupling member consisting of a plurality of parts.

The ratchet 11 can be formed as described in FIGS. 14 and 15 of patent application PCT/CH2007/000243 (U.S. Pat. No. 8,048,037), the disclosure and teaching of which is incorporated herein by reference.

During a delivery process, which is triggered by pressing the push button 15, the indicating drum 4 is rotated back in the opposite direction and is shifted back again in the proximal direction (to the right in FIG. 1) by the threaded engagement with the inner thread 12c of the injection device, wherein the indicating drum 4 can also come to abut the housing of the injection device, e.g. the housing part 12b with effect in the circumferential direction. If a delivery movement is not braked, i.e. if the threaded rod 2 is moved in the distal direction without a counter force, for example when a product container is not inserted, this process can result in the indicating drum 4 or the counter piece 12b being heavily stressed and in an extreme case deformed or even damaged. A braking means (comprising elements 17, 18) which acts on the drive movement is therefore provided.

The coupler K1, which is formed from the coupler member—which is configured as an arresting sleeve 14—and the coupler sleeve 5, serves to couple the coupler sleeve 5, rotationally fixed, to the housing 12 and/or to decouple the coupler sleeve 5 for a rotation relative to the housing 12 switching states. The coupler K1 is decoupled when the product container 27 is being replaced, to be able to slide and/or screw the driven member 2 back in the proximal direction again, and when a product is being delivered, to be able to screw the driven member 2 in the distal direction. The coupler K1 is coupled when the product container is fastened to the drive unit and the activation element 15 is non-activated. The coupler K1 is formed by teeth on the outer side of the coupler sleeve 5 which engage with teeth on the inner side of the arresting sleeve 14. This secures the coupler sleeve 5 against rotating relative to the arresting sleeve 14. The arresting sleeve 14 is mounted in the injection device, secured against rotating and such that it can be axially shifted relative to the housing 12 and the coupler sleeve 5.

During a delivery process, the threaded sleeve 13 is shifted in the distal direction by activating the activation element 15, wherein the threaded sleeve 13 presses onto the bearing 29, which, in this example, is formed as a ball bearing but can also be formed as a simple slide bearing, wherein the bearing 29 presses onto the arresting sleeve 14, thus shifting it in the distal direction for a delivery process, and holds it in the distal position during a delivery process. The coupler member 14 is thus situated distally with respect to the projections of the coupler sleeve 5 for the coupler K1. The coupler K1 is therefore decoupled for the duration of the delivery process.

When the activation element 15 is activated, the couplers K1, K2 and K3 behave as follows: pressing the push button 15, which is positioned on the coupler member 10 and/or drive shaft 7, shifts the coupler member 10—together with the push button 15—and the drive shaft 7 in the distal direction. This couples the coupler K2, such that the drive shaft 7 is secured against rotating with respect to the coupler sleeve 5. The coupler K1 is then decoupled, by shifting the arresting sleeve 14 onto which the threaded sleeve 13, which is connected to the drive shaft 7, presses via the bearing 29 which can be axially shifted. Alternatively, the couplers K1 and K2 can also be switched in the reverse order.

Once K2 has been coupled and K1 has been decoupled, the coupler K3 is also decoupled by shifting the coupler member 10 relative to the dosing button 9. The coupler member 10, which is connected to the drive shaft 7, can be rotated relative to the housing 12 once the coupler K3 has been decoupled. The energy or force stored in the drive spring 3 while increasing the dosage can be transmitted onto the drive shaft 7. A torque is thus applied to the drive shaft 7 and transmitted by means of the coupled coupler K2 onto the coupler sleeve 5 which is rotated together with the drive shaft 7 and transmits this rotational movement onto the driven member 2 which is coupled, rotationally secure, to the coupler sleeve 5. The driven member 2, which in this example is configured as a threaded rod, converts the rotational movement into an axial movement in the distal direction due to the threaded engagement 2a, 6a with the engaging member 6, 26, such that the flange 1, which is provided on the distal end of the threaded rod 2 and can likewise be classed as belonging to the driven member, is moved in the distal direction of the injection device.

Since the threaded sleeve 13 is rotated in the opposite direction when the product is being delivered to when the dosage is being increased, the indicating drum 4 is likewise rotated in the opposite direction to when the dosage is being increased.

When the pre-set product dosage is completely delivered, the delivery process is performed and the driven member 2 is shifted in the distal direction until the aforementioned abutment of the indicating drum 4 which acts in the circumferential direction abuts, when the value which can be read off through the window 12d has been rotated down to zero.

If the user of the device lets go of the activation element 15 while the product is being delivered, the couplers couple in the reverse order to that in which they decouple and/or couple during activating. The delivery of product is interrupted, wherein the value which can be read off through the window 12d is the value which would still have to be delivered for the pre-set dosage to be completely delivered. The delivery of product can be continued by pressing the activation element 15 again, wherein it is possible to stop the delivery again by letting go of the activation element 15 or to wait until the product has been completely delivered.

If there is less product situated in the product container than the maximum dosage indicated on the indicating drum, the injection device shown in this example comprises an additional mechanism or means for limiting the maximum dosage which can be set for the last time to prevent a product dosage from being able to be set which is larger than the amount of product in the product container. To this end, a coupling member 30 is provided which can also be referred to as a runner. The runner 30 at least partially encompasses the coupler sleeve 5 and is in an engagement with the coupler sleeve 5 such that the runner 30 is rotationally fixed relative to the coupler sleeve 5 and can be axially shifted relative to the coupler sleeve 5. A thread of the runner 30 which is formed on its outer circumference also engages with an inner thread of the threaded sleeve 13. This arrangement means that if there is a relative rotation between the threaded sleeve 13 and the coupler sleeve 5, the runner 30 performs an axial movement, wherein if there is no relative rotation, the runner 30 does not perform an axial movement. When setting a product dosage, the threaded sleeve 13 is rotated relative to the coupler sleeve 5, such that the runner 30 moves in the proximal direction. During delivery, by contrast, there is no relative movement between the coupler sleeve 5 and the threaded sleeve 13 due to the coupler engagement of the coupler K2. The runner does not then perform any movement. After the product has been dosed and delivered a number of times, the runner 30 enters into axial abutment with the drive shaft 7, whereby it is no longer possible to further increase the dosage, not even when the indicator (elements 4, 12d) would actually still permit this.

The user can replace the product container 27 with a new product container. To this end, the user removes the product container holder 16 from the drive unit by a rotation relative to the housing 12. When the product container 27 is moved from the fastened position to the unfastened position, when the bayonet lock is unlocked, the engaging member (elements 6, 26) is shifted in the distal direction, together with the driven member 2 and the coupler sleeve 5, relative to the housing 12 and the coupler member 14, thus releasing the coupler K1. The projections of the coupler sleeve 5 which are provided for the coupler K1 and point radially outward are then situated distally with respect to the coupler member 14. A relatively small force which acts in the proximal direction can then be applied to the driven member 2, to its flange, whereby the driven member 2 is screwed into the drive unit. The thread of the driven member 2 is not self-locking. When the driven member 2 is screwed back, the coupler sleeve 5 is rotated relative to the threaded sleeve 13, opposite to when the product is being delivered, thus axially shifting the runner 30 back in the distal direction. The driven member 2 can be screwed back against the force of a spring member, at least over a part of the overall path, wherein said spring member for example attempts to shift the driven member in the distal direction. The spring member can for example act and/or be arranged between the driven member 2 and the drive shaft 7. Other spring members are described further below with respect to FIG. 2. It may be preferred if the force of such a spring member is smaller than the force required for an interaction exerted by the driven member 2 on the product via the piston.

When the product container 27 is removed, the holding member 25—which serves to fix the product container 27 in the product container mounting 16—is shifted in the distal direction by the spring 19 until it enters into abutment with the engaging member. This abutment prevents the spring 19 from not being able to be completely relaxed when the product container 27 is removed. This is advantageous, since the spring 19 should apply enough force, even when a product container 27 is removed, to hold the coupler K3 in a coupler engagement, whereby the activation element 15 also remains in its most proximal position.

Figure 2:
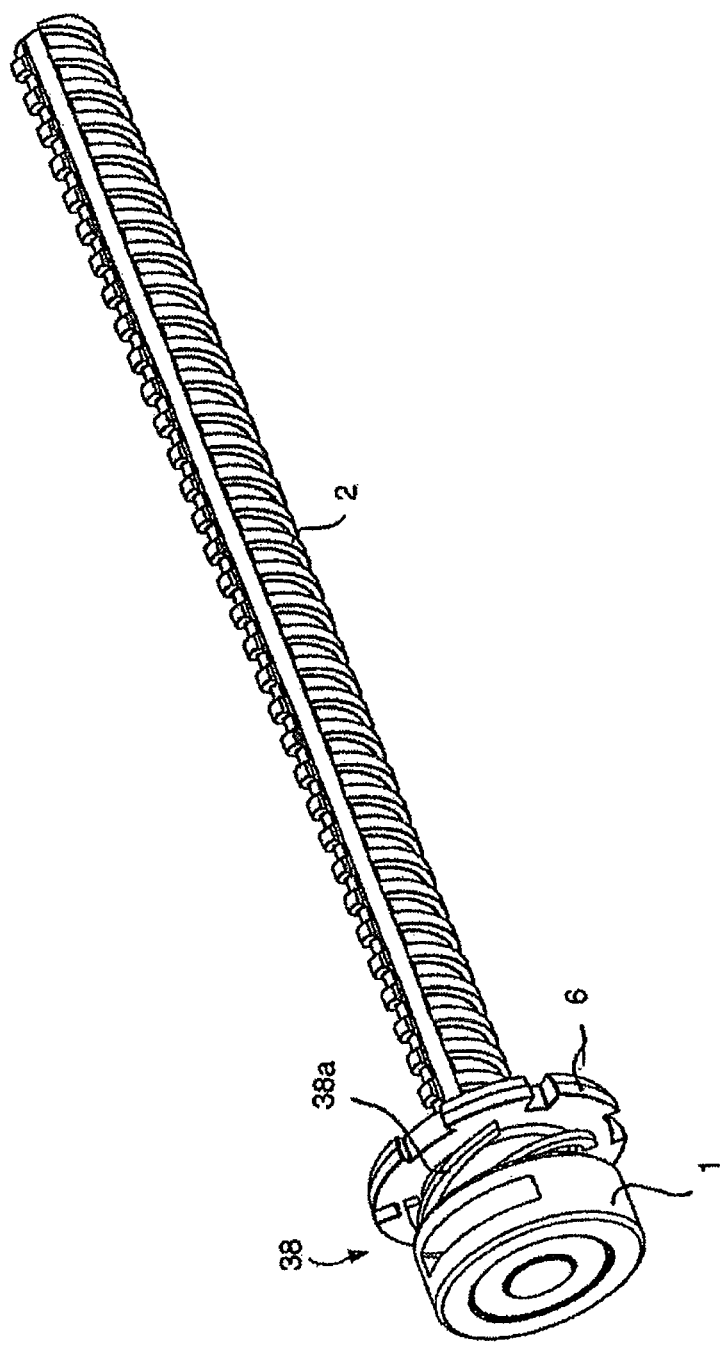
FIG. 2 is a perspective view of a driven member comprising a flange and a spring member.

A spring-loaded flange can be realized in accordance with another aspect of the present invention, as for example shown in FIG. 2.

Once the product container 27, which is configured as an ampoule or a carpoule, has been changed, the user performs so-called venting or priming, as may be described in an operating manual. This is required because on the one hand, air is situated in the product container 27, and on the other, the driven member 2 has been completely slid into the drive unit beforehand and a certain clearance between the piston 28 and the flange 1 has been created by the different fill level of the product container 27.

FIG. 2 shows a driven member 2 comprising a flange 1 which is fastened to the front or distal end of the driven member 2 and is connected, such that it cannot be shifted, to the threaded rod. A spring member 38 is provided between the flange 1 and the threaded insert 6 shown in FIG. 2, wherein said spring member can for example be realised by obliquely projecting spring arms 38a. These spring arms 38a can be fastened to the flange 1 and/or to the threaded insert 6. Equally, an elastomer could also be injection-moulded onto the flange 1 and/or the threaded insert 6. After a new product container 27 has been inserted, there may be a clearance between the flange 1 and the piston 28, which may be due to different fill levels in full product containers 27, which exhibit a certain tolerance.

Once the flange 1, which is connected to the threaded rod 2, has been inserted, the flange 1 directly abuts the threaded insert 6 in accordance with the embodiment shown in FIG. 1.

In accordance with the embodiment shown in FIG. 2, however, the at least one spring member 38 presses the flange 1 away from the threaded insert 6 by a predetermined distance in the distal direction. This enables the flange 1 to always come to rest on the proximal side of the piston 28 when a product container 27 is inserted or when the product container 27 is being inserted, even if the piston 28 is inserted into the product container 27 by a differing distance due to production tolerances in different product containers.

Conventional measures for eliminating the clearance between the flange 1 and the piston 28 are therefore not necessarily required any more and can even for example be omitted.

As can be seen from FIG. 1, the injection device—e.g. the drive unit—comprises a brake (elements 17, 18) which brakes a rotating part—in this example, the transmission element—and/or the drive movement. In conventional injection devices, there is a danger of the components of the injection device being overloaded or even damaged if the device is incorrectly used, for example when the injection device is activated even though a product container has not been inserted. When a product container 27 is inserted, the viscosity of the product when it is being delivered damps the forces and movements which occur. If a product container is missing, then this damping is lacking. This is remedied by the brake in accordance with the present invention which prevents overloading.

Figure 3:
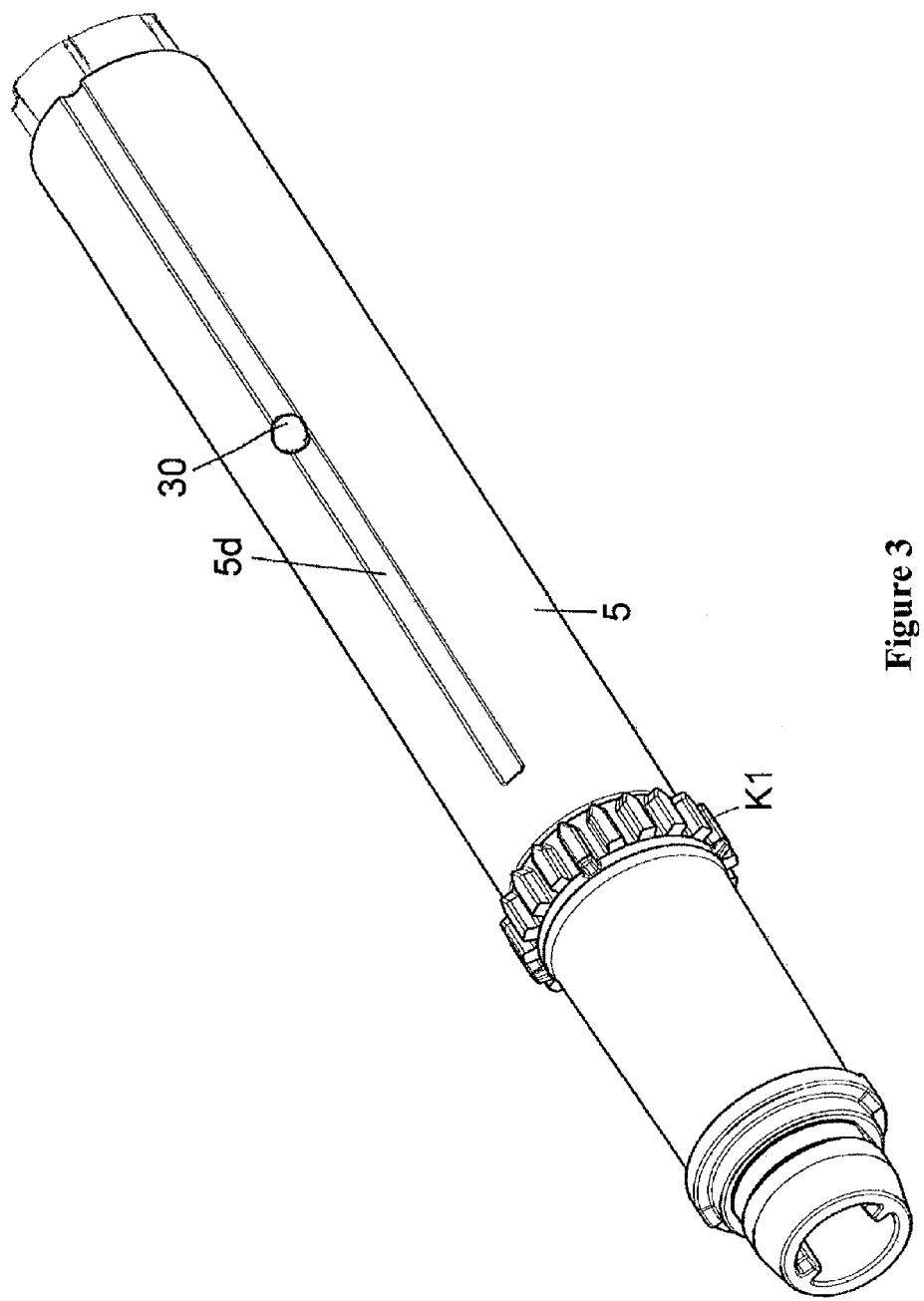
FIG. 3 is a perspective view of a modified coupler sleeve for the device of FIG. 1.

The modified coupler sleeve 5 from FIG. 3—which, like the coupler sleeve 5 from FIG. 1, serves as the second element—is essentially designed in the same way as the coupler sleeve from FIG. 1. The coupler sleeve 5 comprises a guiding track 5d, a longitudinal groove, which extends parallel to the rotational axis about which the coupler sleeve can be rotated. The coupling member 30, which in this example is configured as a sphere, engages with the guiding track. The guiding track 5d has a rounded cross-section and exhibits a radius which approximately corresponds to the radius of the sphere. The sphere 30 is guided parallel to the longitudinal axis of the coupler sleeve 5 by the guiding track 5d. Instead of a sphere, another rotational body such as for example a cylinder could also be guided by the guiding track 5d. The sphere 30 also engages with the guiding track 13b of the threaded sleeve 13 (see for example FIG. 1 or 5), wherein the guiding track is configured as a thread and the threaded sleeve 13 serves as the first element. The guiding track 13b can likewise have a rounded cross-section, in the same way as the guiding track 5d.

Figure 4:
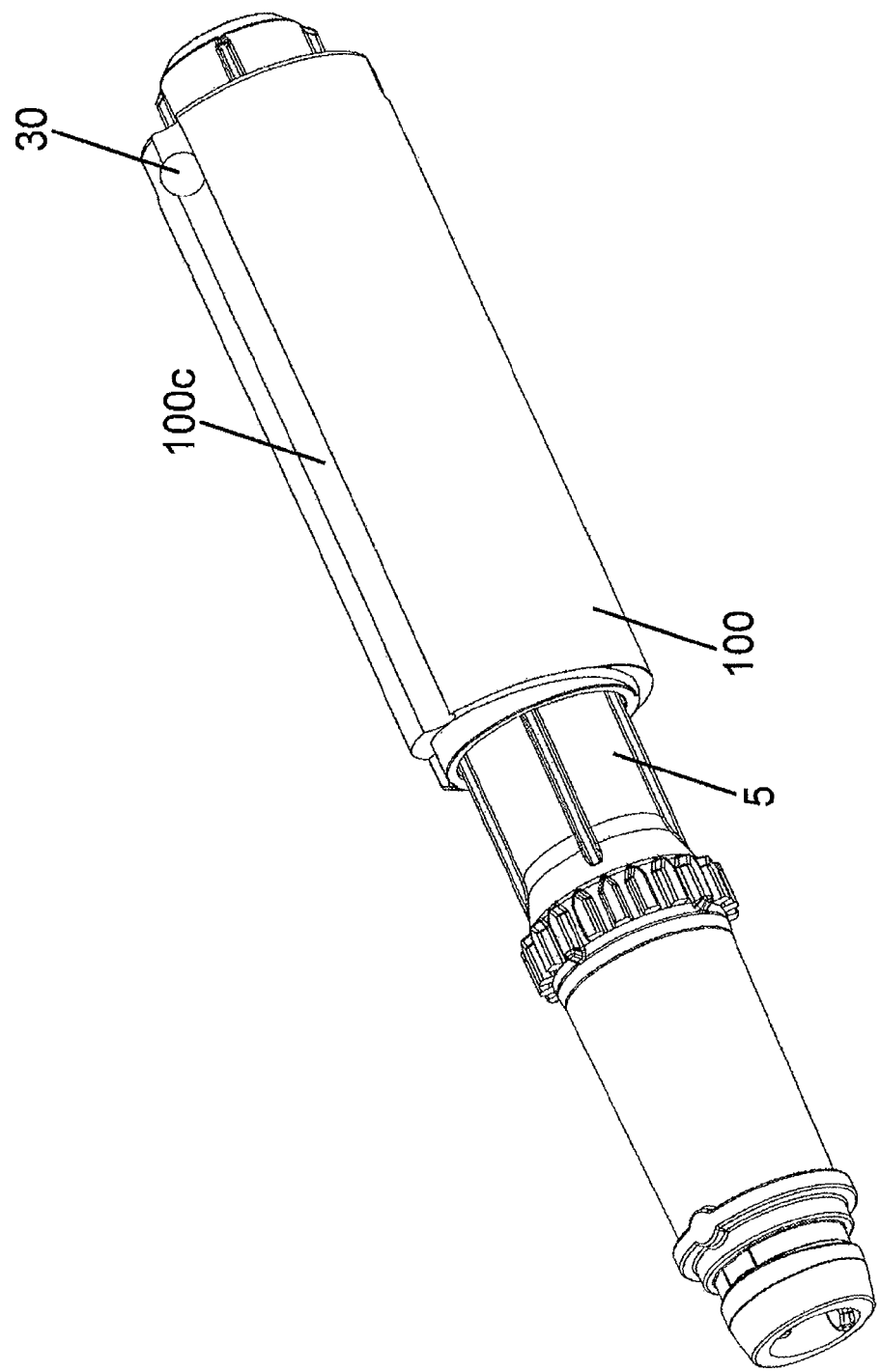
FIG. 4 is a perspective view of another modification of the device of FIG. 1.
Figure 5:
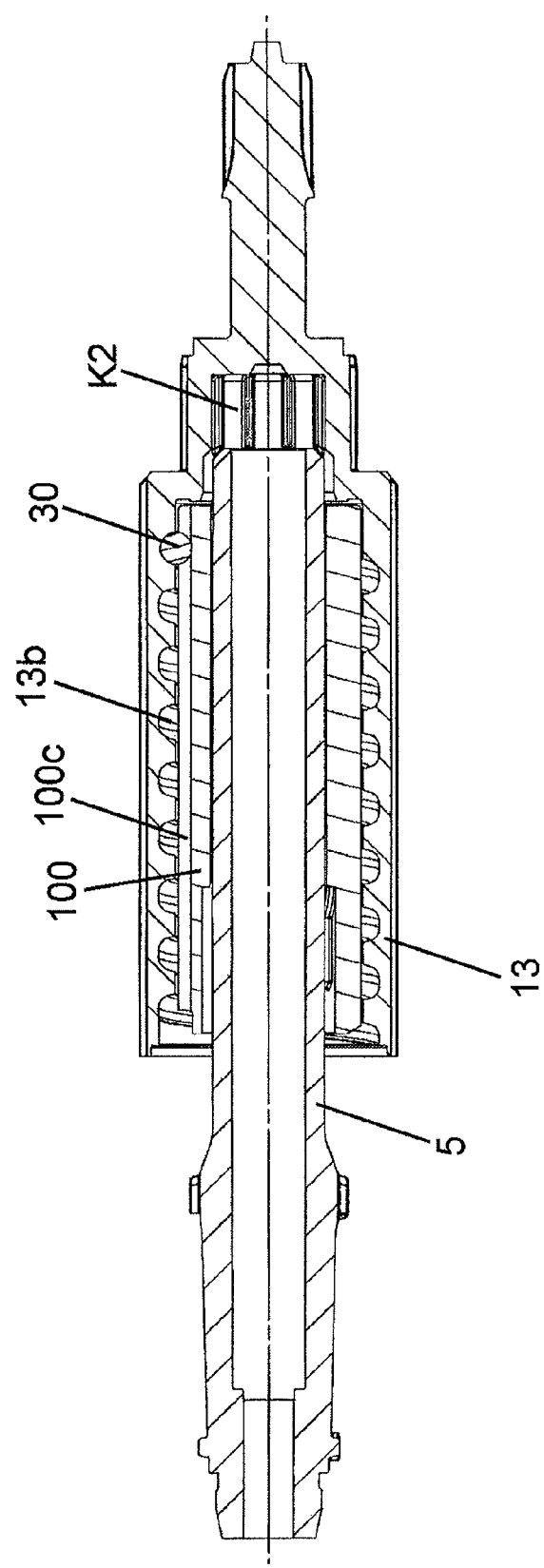
FIG. 5 is a cross-sectional view showing the modification of FIG. 4.

The modification shown in FIGS. 4 and 5 corresponds in principle to the embodiment of FIG. 3, wherein the guiding track 100c for the sphere 30 is not formed by the coupler sleeve 5 but rather by an intermediate sleeve 100, i.e. on its outer circumference. The intermediate sleeve 100 is connected, rotationally fixed and such that it can be axially shifted, to the coupler sleeve 5 and is rotationally fixed relative to the coupler sleeve 5 and can be axially shifted relative to the coupler sleeve 5, such as in this example via longitudinal guides which are formed on the outer circumference of the coupler sleeve 5 and engage with the projections formed on the inner circumference of the intermediate sleeve 100.

An advantage of the intermediate sleeve 100 in all the modifications shown here is on the one hand that it can be placed onto the coupler sleeve 5 from FIG. 1 and on the other that when the product container is being replaced, the intermediate sleeve 100 does not need to perform a longitudinal movement, since the coupler sleeve 5 can be longitudinally moved relative to the intermediate sleeve 100.

In the embodiments of FIGS. 3 to 5, the threaded sleeve 13 is rotated relative to the coupler sleeve 5, the coupling member 30 and, as applicable, the intermediate sleeve 100 when the dosage is being set, wherein the coupling member 30 is rotationally fixed relative to the coupler sleeve 5 or the intermediate sleeve 100 and performs a longitudinal movement along the guiding track 5*d* or 100*c*. "Rotationally fixed" refers to the rotation of the sphere 30 relative to the longitudinal axis of the coupler sleeve 5 or intermediate sleeve 100 and not to the ability of the sphere 30 to rotate about its center point. In its stop position, the sphere 30 enters into abutment with the end of the guiding track 13*b* and the flank of the longitudinal guide 5*d* or 100*c*, thus preventing a dosage from being increased.

Figure 6:
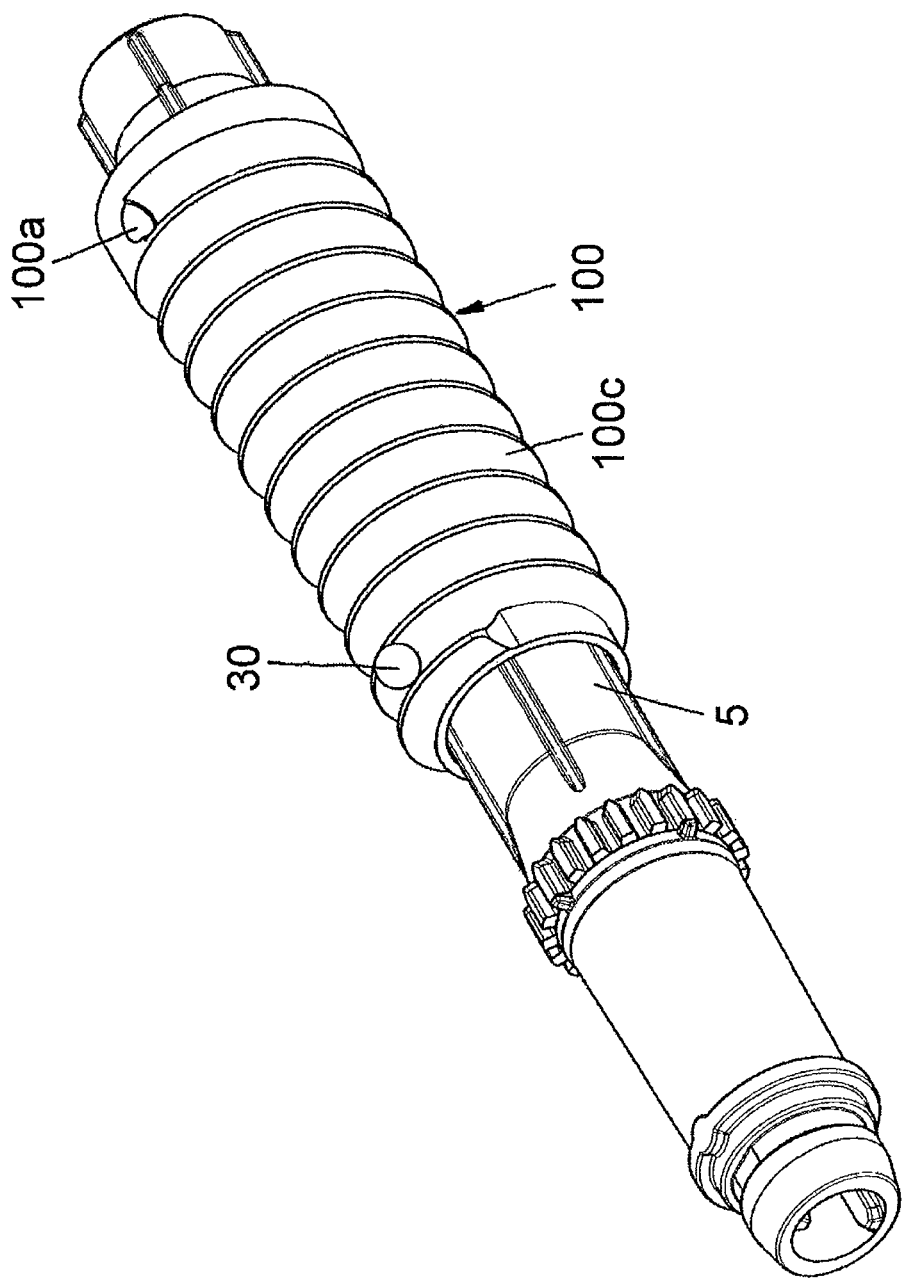
FIGS. 6 and 7 are perspective views of another modification of the device of FIG. 1.
Figure 7:
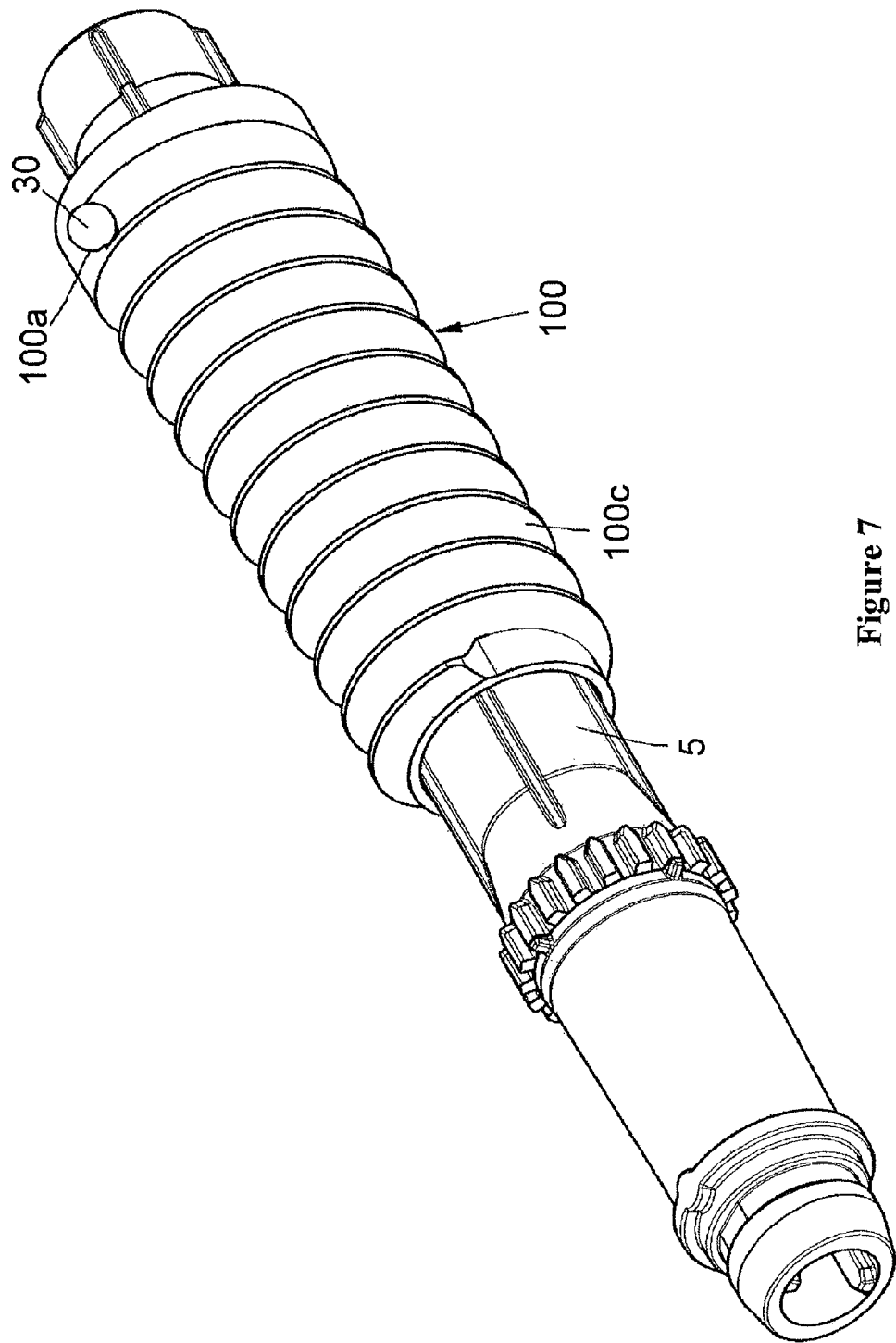
Figure 8:
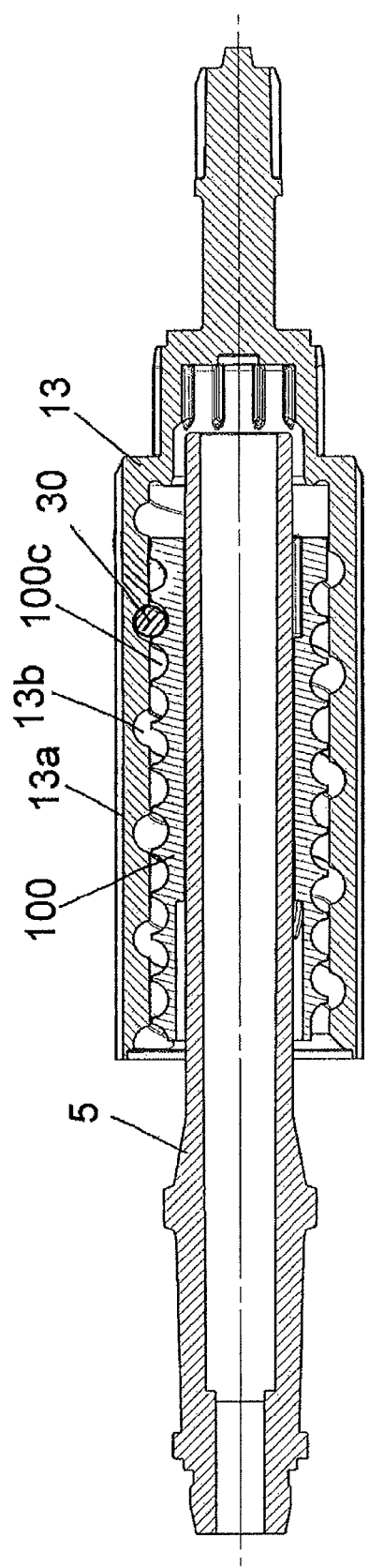
FIG. 8 is a cross-sectional view showing the modification of FIGS. 6 and 7.

The modification shown in FIGS. 6 to 8 comprises an intermediate sleeve 100 which is connected to the coupler sleeve 5 in the same way as the intermediate sleeve 100 of FIGS. 4 and 5 and which comprises a guiding track 100*c* which extends along the longitudinal axis in the shape of a thread or helically, instead of a guiding track 100*c* which extends parallel to the longitudinal axis. The thread-shaped or helical guiding track 100*c* exhibits a smaller pitch than the thread-shaped or helical guiding track 13*b* of the threaded sleeve 13. The guiding track 100*c* exhibits a direction of rotation which is opposite to the guiding track 13*b*. As can be seen from FIG. 8, the sphere 30 is arranged where the guiding tracks 13*b* and 100*c* intersect and form an enclosure for the sphere 30. At the point where they intersect, the guiding tracks 13*b* and 100*c* form an enclosure which is rhombic in its projection and in which the sphere is guided with a clearance.

When the threaded sleeve 13 is rotated relative to the intermediate sleeve 100, the sphere 30 is rotated continuously along with the threaded sleeve 13, but at a lower angular speed than the threaded sleeve 13. The mechanism is space-saving due to the geared-down movement of the sphere 30.

Each time the dosage is increased, the sphere 30—which is situated in the position shown in FIG. 6 when a product container is full—is moved in the direction of the stop abutment 100*a*, which is formed by the end of the thread 100*c*, by a distance which corresponds to the dosage set. In FIG. 7, the sphere is situated in its stop position, i.e. in abutment with the stop abutment 100*a*. When the sphere is in the position shown in FIG. 7, the end of the guiding track 13*c* is likewise in abutment with the sphere 30, i.e. opposite the abutment 100*a*, wherein the threaded sleeve 13 has been left out in FIG. 7 for illustrative purposes.

Figure 9:
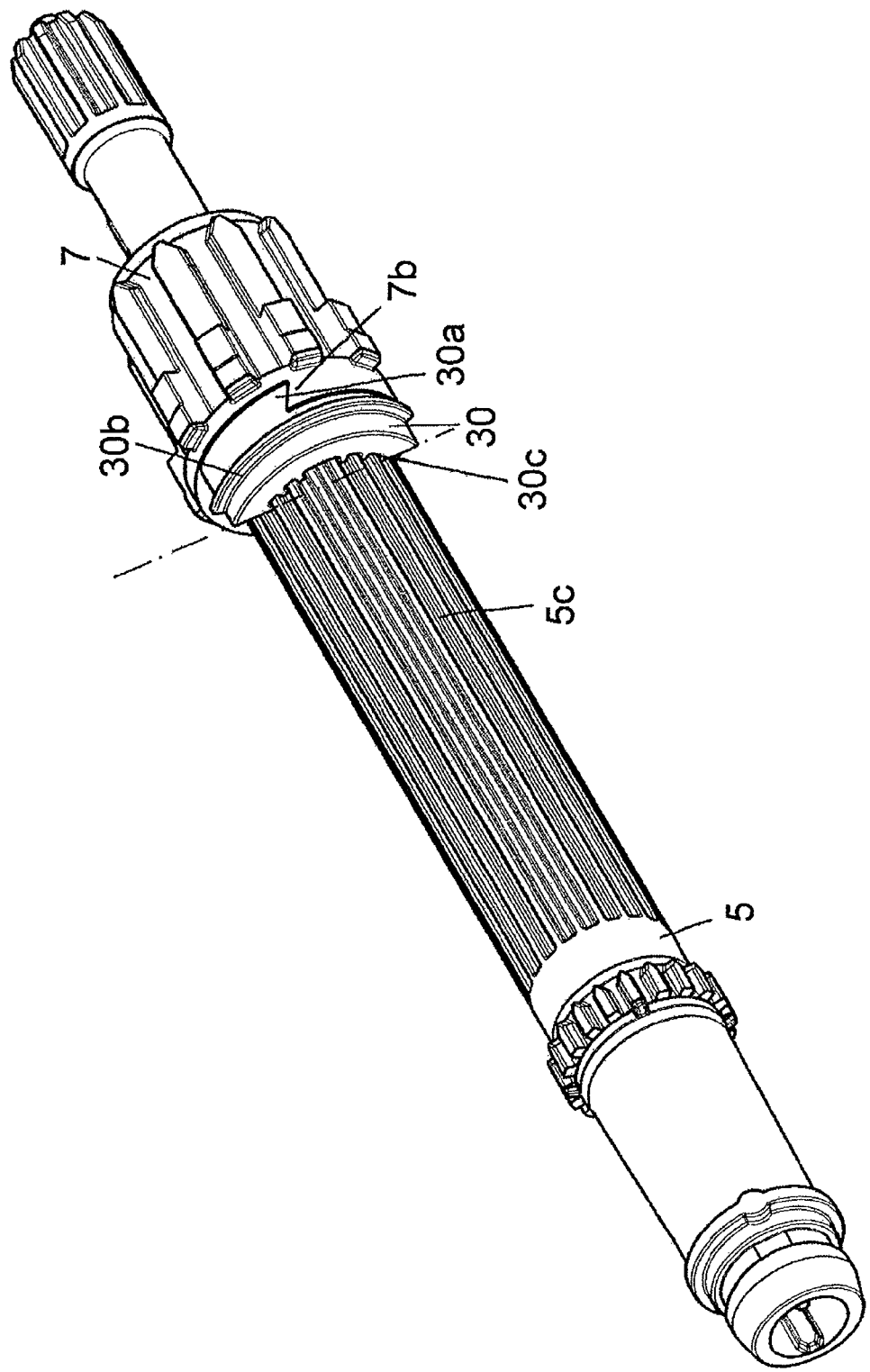
FIGS. 9 and 10 are perspective views of another modification of the device of FIG. 1.
Figure 10:
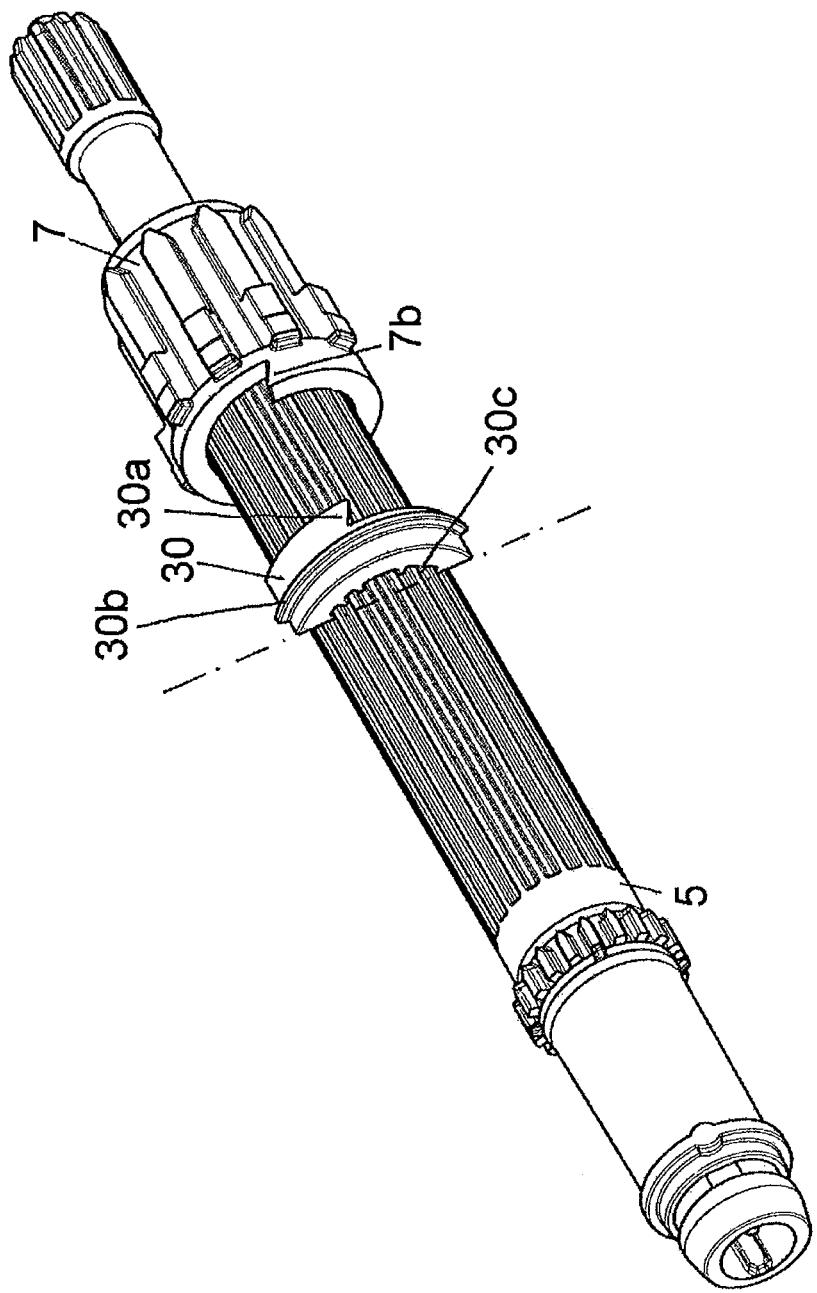
Figure 11:
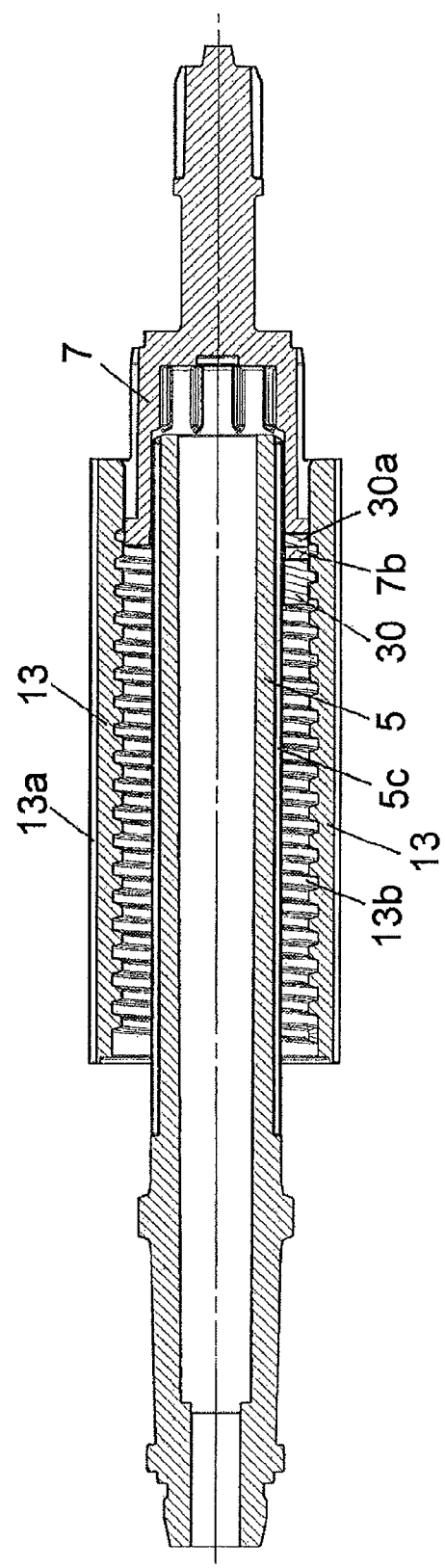
FIG. 11 is a cross-sectional view showing the modification from FIGS. 9 and 10.

FIGS. 9 to 11 show a modification for the device of FIG. 1, comprising a coupling member which is configured as a segment 30, wherein projections 30*c* of the segment 30 engage with longitudinal guides 5*c* of the coupler sleeve 5. The segment 30 is rotationally fixed relative to the coupler sleeve 5 and can be longitudinally moved relative to the coupler sleeve 5. The outer circumference of the segment 30 comprises a threaded portion 30*b* which engages with the thread 13*b*. When a dosage is being increased, the segment 30 is moved in the direction of the stop position which is shown in FIG. 9 and in which an abutment 7*b* is in engagement with the abutment 30*a*, thus preventing the drive shaft 7 and the threaded sleeve 13 connected to it from rotating relative to the coupler sleeve 5 and the segment 30. The abutments 7*b*, 30*a* comprise abutment surfaces which are arranged transverse to the longitudinal direction, wherein the segment 30 is drawn towards the drive shaft 7 by their shape. The rotational abutment which acts in the circumferential direction is highly stable due to the shape of the correspondingly inclined abutment surfaces.

The segment comprises two ends in the circumferential direction which are connected in each of FIGS. 9 and 10 to a connecting straight line which is indicated as a dot-dash line. This imaginary connecting straight line intersects the coupler sleeve 5 but does not intersect the piston rod 2 accommodated in the coupler sleeve 5 but rather passes it or is tangential to it.

The annular gap between the threaded sleeve 13 and the coupler sleeve 5 is not entirely filled, hence the segment 30 is space-saving.

Figure 12:
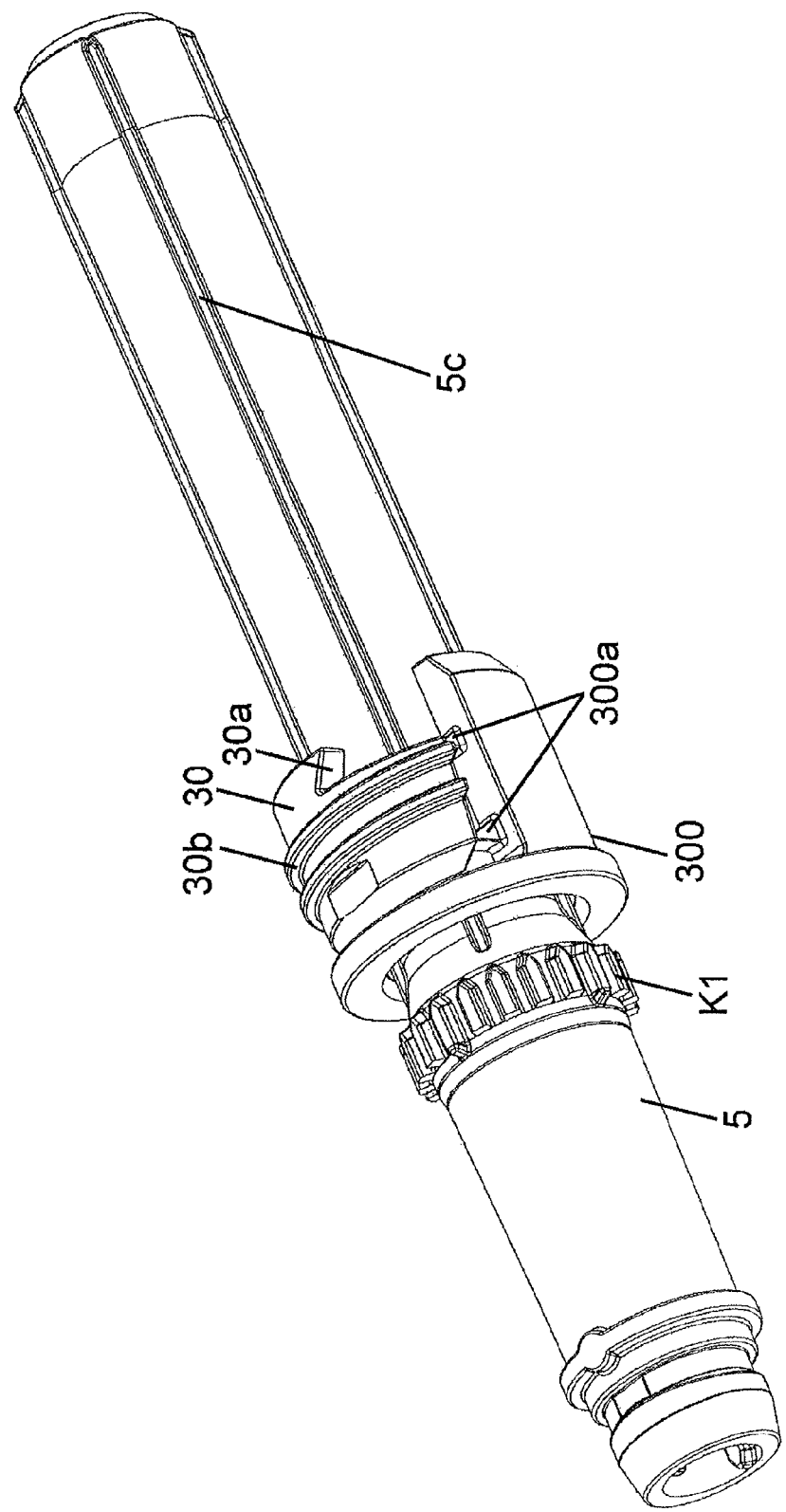
FIG. 12 is a perspective view of a development of the modification of FIGS. 9-11.

The segment 30 shown in FIG. 12 is an advantageous development of the segment of FIGS. 9 to 11 and is also designed in the same way in principle. However, the segment 30 is formed on a base element 300 in a material fit comprising a plurality of predetermined breaking points 300*a*. During installation, the part which is formed in one part from the segment 30 and the base element 300 is affixed to the coupler sleeve 5, wherein the base element 300—as also the segment 30—is secured against rotating via the longitudinal guides 5*c*. Unlike the segment 30, however, the base element is axially fixed relative to the coupler sleeve 5. When a dosage is being set, e.g. when a dosage is being increased, the segment 30 is axially shifted relative to the base element 300 in the direction of the stop position, thus breaking the predetermined breaking points 300*a*. The base element 300 advantageously enables the segment 30 to be easily installed. The base element 300 forms a sleeve portion, one part of which is the segment 30. The part of the sleeve portion which remains on the base element 300 can form a supporting member which supports the coupler sleeve 5 against a movement transverse to the longitudinal axis.

Figure 13:
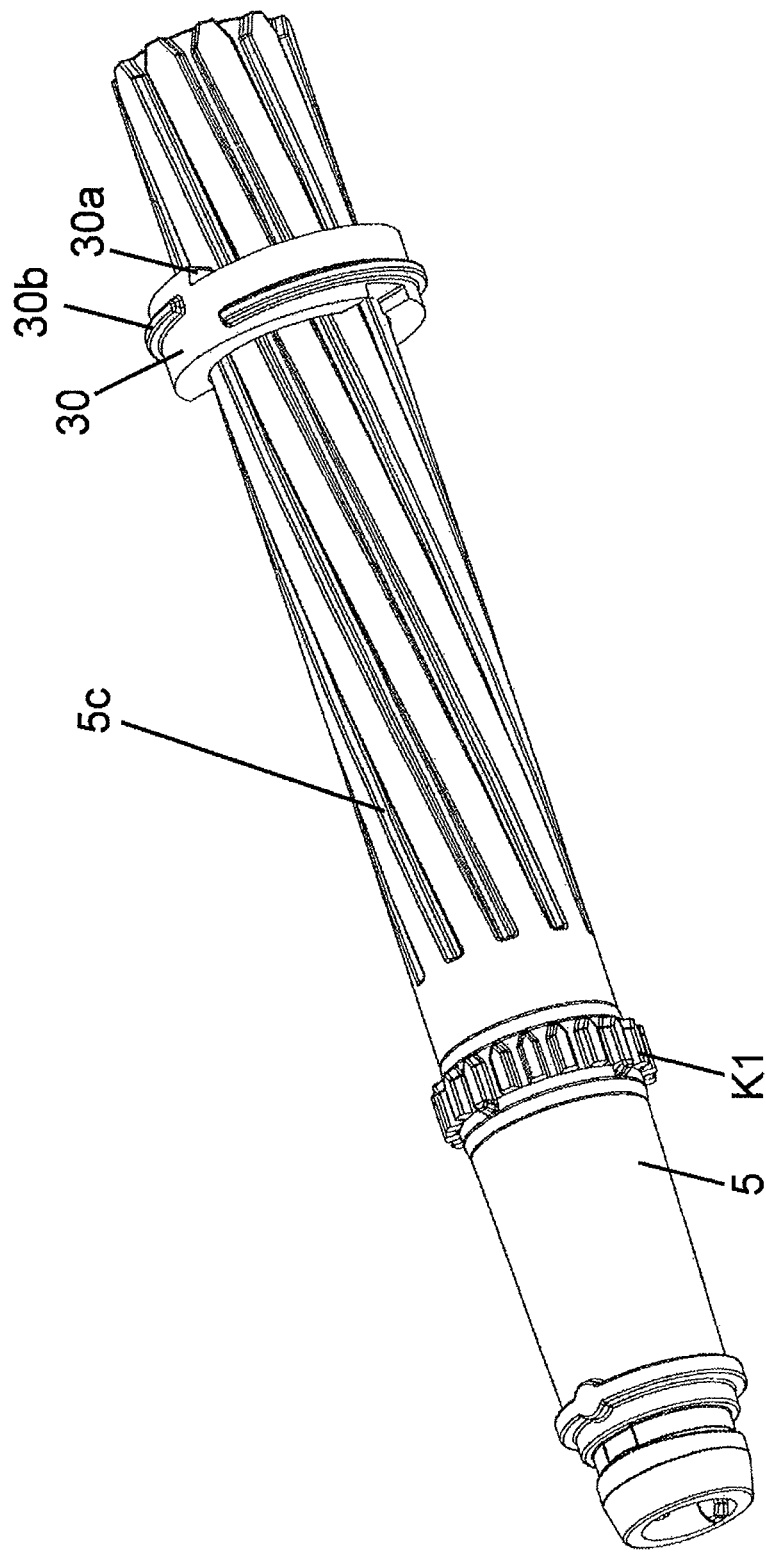
FIG. 13 is a perspective view of another modification of the device of FIG. 1.

FIG. 13 shows a coupling member in the form of a nut 30 which completely surrounds the coupler sleeve 5, i.e. forms a passage. A segment could for example be provided instead of the nut 30, since aside from the fact that it forms a closed ring, the nut is similar in concept to the segment of FIGS. 9 to 11. The coupler sleeve 5 from FIG. 13, however, comprises a thread-shaped guiding track 5*c* which exhibits the opposite direction of rotation to the threaded portion 30*b* and a greater pitch than the threaded portion 30*b* which engages with the thread 13*b* of the threaded sleeve 13. Due to this arrangement, the nut 30 is continuously rotated along with the threaded sleeve when the dosage is being set, wherein the nut 30 exhibits a lower rotational angular speed than the threaded sleeve 13. The mechanism is space-saving due to this gearing decrease.

The coupler sleeve 5 of FIG. 14 comprises a guiding track 5*c* which becomes wider in the proximal direction and can, for example, be used together with a nut-shaped coupling member such as the coupling member from FIG. 13. The expanding guiding track 5*c* makes it easier to remove the coupler sleeve 5 from the die of an injection-moulding tool. The guiding track 5*c*, which is groove-shaped, is limited on both sides by a flank in each case, wherein at least one flank extends helically over the circumference. The other flank can likewise extend helically over the circumference or can be arranged approximately parallel to the longitudinal axis of the coupler sleeve 5. This combines advantages of the modifications of FIGS. 13 and 14, such that the coupler sleeve 5 can be easily removed from a die, and the stop nut 30—which abuts the helically extending flank when a dosage is being increased—performs a continuous and geared-down rotational movement when the coupler sleeve 5 is rotated.

When a dosage is being corrected, or during at least a part of the dosage correction, the stop nut 30 in the embodiment of FIG. 14 does not need to be moved in the reverse order of movement to when a dosage is being increased, since the distance between the helical flank and the flank which runs parallel to the longitudinal axis of the coupler sleeve increases in the proximal direction as the path increases. This creates a gap between at least one of the flanks and the part of the coupling member 30 which engages with the guiding track 5*c*, wherein said gap increases as the path increases.

FIG. 15 shows a coupling member which consists of a plurality of parts, e.g. two parts, and comprises a guiding part 30m and an abutment part 30n which can be rotated relative to the guiding part 30m and is axially fixed relative to the guiding part 30m. The guiding part is longitudinally guided on the second element and engages with the thread of the first element. The abutment part 30n comprises an abutment 30a which acts in the circumferential direction. A ratchet 301 is arranged between the guiding part 30m and the abutment part 30n and produces tangible and audible clicks when the guiding part 30m is rotated relative to the abutment part 30n. i.e. when the abutment 30a is in a corresponding counter abutment, as for example indicated in FIG. 9 by the reference character 7b. This indicates to the user that the stop position has been reached when the final dosages contained in the product container have been reached. The guiding part 30m and the abutment part 30n can optionally be rotationally biased against each other using a spring (not shown).

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. For example, it should be appreciated any feature, embodiment, structure, operation, method and/or component of the present invention may be implemented separately or in combination with any other feature, embodiment, structure, operation, method and/or component. All such modifications and variations are within the scope of the invention as determined by the appended claims when interpreted in accordance with the breadth they are fairly, legally, and equitably entitled.

The invention claimed is:

1. An injection device, comprising:
   a) a dosage setting element and a first element which is coupled to the dosage setting element and can be rotated relative to a second element when a dosage is being set and is rotationally fixed relative to the second element when a dosage is being delivered, wherein the first element and the second element are coupled via a coupling member; and
   a stop abutment, wherein when a dosage is being set, the coupling member performs a movement toward a stop position, and wherein the coupling member is a sphere arranged between the first element and the second element and prevents a dosage from being set when in the stop position.

2. The injection device according to claim 1, wherein the first element and the second element are arranged concentrically with respect to each other with an annular gap between them and the coupling member is arranged between the first element and the second element in the annular gap.

3. The injection device according to claim 1, wherein the coupling member engages with a guiding track which is an inner thread of the first element and with a guiding track which is an outer thread of the second element.

4. The injection device according to claim 1, wherein when the first element is rotated relative to the second element, the coupling member is rotated along with the first element by a rotational angle which is either greater or smaller than the rotational angle of the first element.

5. The injection device according to claim 1, wherein the first element is coupled, rotationally fixed, to at least one of a dosage indicating sleeve and a torsion spring.

6. The injection device according to claim 1, wherein at least one of the first element and the second element are sleeve-shaped.

7. The injection device according to claim 1, wherein a supporting member is arranged opposite the coupling member in relation to the circumference of the second element.

8. The injection device according to claim 1, wherein the coupling member is coupled to the first element and to the second element such that when the first element is moved relative to the second element, the coupling member can be or is rotated relative to at least one or both of the first element and the second element.

9. The injection device according to claim 8, wherein the coupling member engages with a longitudinal guide which is formed on one of the first element and the second element and with a thread-shaped guiding track which is formed on the other of the first element and the second element.

10. The injection device according to claim 1, wherein the second element is coupled, rotationally fixed, to a driven member, wherein the driven member can be screwed in a delivery direction to deliver a product.

11. The injection device according to claim 10, wherein the driven member comprises a piston rod.

12. The injection device according to claim 10, wherein the coupling member is a sphere arranged in an annular gap between the first element and the second element.

13. The injection device according to claim 1, wherein the first element and the second element each comprises a guiding track with which the coupling member sphere engages by its arrangement in the guiding tracks and in an annular gap between the first element and the second element.

14. The injection device according to claim 13, wherein the guiding tracks the coupling member sphere engages are configured to be thread-shaped or helical or as a longitudinal guide which runs approximately parallel to a longitudinal direction of the injection device or a rotational axis of the first element or second element.

15. The injection device according to claim 14, wherein at least one of the guiding tracks the coupling member sphere engages is concave and/or rounded and/or approximately circular in cross-section.

16. The injection device according to claim 1, wherein at least one of the first element and the second element comprises a thread-shaped guiding track, and the other of the first element and the second element comprises a guiding track which is thread-shaped or which extends parallel to the longitudinal axis of the injection device, the guiding tracks intersecting and the coupling member having a center of gravity where the guiding tracks intersect.

17. The injection device according to claim 16, wherein the guiding tracks form an enclosure for the coupling member which encloses the coupling member at least such that it remains where the guiding tracks intersect.

18. The injection device according to claim 17, wherein at least one of the guiding tracks is concave, rounded or approximately circular in cross-section.

19. The injection device according to claim 18, wherein at least one of the guiding tracks forms an abutment for the coupling member, the abutment acting in either the axial direction or circumferential direction for the coupling member.

* * * * *